US012239739B2

(12) United States Patent
Nielsen et al.

(10) Patent No.: US 12,239,739 B2
(45) Date of Patent: *Mar. 4, 2025

(54) ORAL DOSING OF GLP-1 COMPOUNDS

(71) Applicant: Novo Nordisk A/S, Bagsvaerd (DK)

(72) Inventors: Flemming S. Nielsen, Frederikssund (DK); Per Sauerberg, Farum (DK)

(73) Assignee: Novo Nordisk A/S, Bagsvaerd (DK)

(*) Notice: Subject to any disclaimer, the term of this patent is extended or adjusted under 35 U.S.C. 154(b) by 0 days.

This patent is subject to a terminal disclaimer.

(21) Appl. No.: 16/361,971

(22) Filed: Mar. 22, 2019

(65) Prior Publication Data
US 2019/0216739 A1 Jul. 18, 2019

Related U.S. Application Data

(63) Continuation of application No. 15/651,043, filed on Jul. 17, 2017, now Pat. No. 10,278,923, which is a continuation of application No. 14/785,493, filed as application No. PCT/EP2014/058974 on May 2, 2014, now abandoned.

(30) Foreign Application Priority Data

May 2, 2013 (EP) .................................. 13166205

(51) Int. Cl.
| A61K 38/26 | (2006.01) |
| A61K 9/00 | (2006.01) |
| A61K 9/20 | (2006.01) |
| A61P 3/04 | (2006.01) |
| A61P 3/10 | (2006.01) |
| A61K 31/166 | (2006.01) |

(52) U.S. Cl.
CPC .......... *A61K 9/2013* (2013.01); *A61K 9/0053* (2013.01); *A61K 38/26* (2013.01); *A61P 3/04* (2018.01); *A61P 3/10* (2018.01); A61K 9/2054 (2013.01); A61K 31/166 (2013.01)

(58) Field of Classification Search
None
See application file for complete search history.

(56) References Cited

U.S. PATENT DOCUMENTS

| 5,545,618 A | 8/1996 | Buckley et al. |
| 5,574,010 A | 11/1996 | McFadden |
| 5,604,203 A | 2/1997 | Balasubramaniam |
| 5,773,647 A | 6/1998 | Leone-Bay et al. |
| 5,866,536 A | 2/1999 | Leone-Bay et al. |
| 5,968,899 A | 10/1999 | Sekine et al. |
| 6,046,167 A | 4/2000 | Balasubramaniam |
| 6,071,510 A | 6/2000 | Leone-Bay et al. |
| 6,268,343 B1 | 7/2001 | Knudsen et al. |
| 6,348,447 B1 | 2/2002 | Hellstrom et al. |
| 6,458,924 B2 | 10/2002 | Knudsen et al. |
| 6,514,500 B1 | 2/2003 | Bridon et al. |
| 7,049,283 B2 | 5/2006 | Ault et al. |
| 7,235,627 B2 | 6/2007 | Knudson et al. |
| 7,271,149 B2 | 9/2007 | Glaesner et al. |
| 7,417,028 B2 | 8/2008 | Ewing et al. |
| 7,829,123 B2 | 11/2010 | Sundholm et al. |
| 8,022,035 B2 | 9/2011 | Schwartz et al. |
| 8,039,018 B2 | 10/2011 | Majuru et al. |
| 8,053,429 B2 | 11/2011 | Cumming et al. |
| 8,097,698 B2 | 1/2012 | Knudsen et al. |
| 8,536,122 B2 | 9/2013 | Lau et al. |
| 8,648,041 B2 | 2/2014 | Garibay et al. |
| 8,895,694 B2 | 11/2014 | Spetzler et al. |
| 8,901,073 B2 | 12/2014 | Bloom |
| 9,067,977 B2 | 6/2015 | Spetzler et al. |
| 9,085,637 B2 | 7/2015 | Oestergaard et al. |
| 9,186,392 B2 | 11/2015 | Klein et al. |
| 9,266,940 B2 | 2/2016 | Wieczorek et al. |
| 9,278,123 B2* | 3/2016 | Sauerberg ............ A61K 9/2013 |
| 9,527,900 B2 | 12/2016 | Linderoth et al. |
| 9,993,430 B2* | 6/2018 | Jensen ................. A61K 9/2077 |
| 10,005,827 B2 | 6/2018 | Spetzler et al. |
| 10,086,047 B2* | 10/2018 | Sauerberg ................. A61P 9/00 |
| 10,246,497 B2 | 4/2019 | Oestergaard et al. |
| 10,278,923 B2* | 5/2019 | Nielsen ................ A61K 9/0053 |
| 10,335,369 B2 | 7/2019 | Vilhelmsen |
| 10,933,120 B2* | 3/2021 | Vilhelmsen ............... A61P 3/00 |
| 10,960,052 B2* | 3/2021 | Sauerberg ............... A61P 25/28 |
| 11,382,957 B2* | 7/2022 | Sauerberg ................. A61P 3/10 |
| 2001/0011071 A1 | 8/2001 | Knudsen et al. |
| 2002/0141985 A1 | 10/2002 | Pittner et al. |
| 2005/0009748 A1 | 1/2005 | Dinh et al. |
| 2005/0148497 A1 | 7/2005 | Khan |

(Continued)

FOREIGN PATENT DOCUMENTS

| CN | 1190893 A | 8/1998 |
| CN | 1487825 A | 4/2004 |

(Continued)

OTHER PUBLICATIONS

GenScript, "Peptide YY (PYY) (3-36), human," https://www.genscript.com/peptide/RP10354-Peptide_YY_PYY_3_36_human.html, accessed Jan. 27, 2020.
National Institute of Diabetes and Digestive and Kidney Diseases,"Prescription Medications to Treat Overweight and Obesity," Jul. 2016, 10 pages, retrieved on Apr. 13, 2020, URL: https://www.niddk.nih.gov/health-information/weight-management/prescription-medications-treat-overweight-obesity.
W.K. Sietsema, "The absolute oral bioavailability of selected drugs." Mar. 1989, International Journal of Clinical Pharmacology, Therapy and Toxicology, vol. 27, No. 4, pp. 179-211.
Declaration of Doctor Peter Rue, for EP2827885 dated Jul. 29, 2020.
Declaration of Professor Leon Aarons for EP2827885 dated Jul. 29, 2020.
Shajahan et al., A flexible technology for modified-release drugs: Multiple-unit pellet system (MUPS) May 2009, Journal of Controlled Release, vol. 147, No. 1, pp. 2-16.

(Continued)

Primary Examiner — Brian Gangle
Assistant Examiner — Andrea K McCollum
(74) Attorney, Agent, or Firm — Leon Y. Lum

(57) ABSTRACT

The present invention relates to improved uses of glucagon-like peptide-1 (GLP-1) peptides in oral therapy.

27 Claims, No Drawings

(56) References Cited

U.S. PATENT DOCUMENTS

| | | |
|---|---|---|
| 2005/0176630 A1 | 8/2005 | Cowley et al. |
| 2006/0078622 A1 | 4/2006 | Majuru et al. |
| 2006/0078623 A1 | 4/2006 | Dhoot et al. |
| 2006/0135747 A1 | 6/2006 | Levy et al. |
| 2006/0211610 A1 | 9/2006 | Dong |
| 2006/0286129 A1 | 12/2006 | Sarubbi |
| 2007/0049557 A1 | 3/2007 | Ahmed et al. |
| 2007/0135351 A1 | 6/2007 | Conde-Knape et al. |
| 2007/0197445 A1 | 8/2007 | Balasubramaniam |
| 2007/0203058 A1 | 8/2007 | Lau et al. |
| 2007/0224262 A1 | 9/2007 | Majuru et al. |
| 2008/0076705 A1 | 3/2008 | Kodra et al. |
| 2008/0153779 A1 | 6/2008 | Liao et al. |
| 2008/0194486 A1 | 8/2008 | Bridon et al. |
| 2008/0194676 A1 | 8/2008 | Abbas et al. |
| 2008/0207507 A1 | 8/2008 | Lau et al. |
| 2008/0221038 A1 | 9/2008 | Balasubramaniam |
| 2008/0255250 A1 | 10/2008 | Gomez-Orellana et al. |
| 2008/0269114 A1 | 10/2008 | Schwartz |
| 2009/0088369 A1 | 4/2009 | Steiness |
| 2009/0099074 A1 | 4/2009 | Bridon et al. |
| 2009/0111730 A1 | 4/2009 | Dorwald et al. |
| 2009/0124639 A1 | 5/2009 | Oyewumi et al. |
| 2009/0143330 A1 | 6/2009 | Levchik et al. |
| 2009/0156478 A1 | 6/2009 | Lau et al. |
| 2009/0186811 A1 | 7/2009 | Schwartz |
| 2009/0215682 A1 | 8/2009 | Moore et al. |
| 2010/0016229 A1 | 1/2010 | Sarubbi |
| 2010/0069307 A1 | 3/2010 | Danho et al. |
| 2010/0069410 A1 | 3/2010 | Majuru et al. |
| 2010/0151009 A1 | 6/2010 | Levchik |
| 2010/0210526 A1 | 8/2010 | Joshi |
| 2010/0239658 A1 | 9/2010 | Majuru et al. |
| 2010/0292133 A1 | 11/2010 | Spetzler et al. |
| 2010/0331245 A1 | 12/2010 | Dong |
| 2011/0142800 A1 | 6/2011 | Kidron et al. |
| 2011/0144008 A1 | 6/2011 | Larsen et al. |
| 2011/0166321 A1 | 7/2011 | Garibay et al. |
| 2011/0218148 A1 | 9/2011 | Azria et al. |
| 2011/0275559 A1 | 11/2011 | Ostergaard et al. |
| 2012/0040893 A1 | 2/2012 | Cowley et al. |
| 2013/0040877 A1 | 2/2013 | Kofoed et al. |
| 2013/0053311 A1 | 2/2013 | Kalthoff et al. |
| 2013/0096055 A1 | 4/2013 | Kofoed et al. |
| 2013/0240587 A1 | 9/2013 | Buchhalter |
| 2013/0345134 A1 | 12/2013 | Sauerberg et al. |
| 2014/0011732 A1 | 1/2014 | Spetzler et al. |
| 2014/0296131 A1 | 10/2014 | Spetzler et al. |
| 2015/0025003 A1 | 1/2015 | Spetzler et al. |
| 2015/0031606 A1 | 1/2015 | Vilhelmsen |
| 2015/0072926 A1 | 3/2015 | Vilhelmsen et al. |
| 2015/0141336 A1 | 5/2015 | Joergensen et al. |
| 2015/0150811 A1 | 6/2015 | Jensen et al. |
| 2016/0067184 A1 | 3/2016 | Nielsen et al. |
| 2016/0151462 A1 | 6/2016 | Sauerberg et al. |
| 2016/0263197 A1 | 9/2016 | Oestergaard et al. |
| 2016/0289283 A1 | 10/2016 | Oestergaard et al. |
| 2017/0312225 A1 | 11/2017 | Nielsen et al. |
| 2017/0313750 A1 | 11/2017 | Oestergaard et al. |
| 2018/0021272 A1 | 1/2018 | Burshtein et al. |
| 2018/0028622 A1 | 2/2018 | Burshtein et al. |
| 2018/0036234 A1 | 2/2018 | Burshtein et al. |
| 2018/0036382 A1 | 2/2018 | Burshtein et al. |
| 2018/0050096 A1 | 2/2018 | Burshtein et al. |
| 2018/0235888 A1 | 8/2018 | Jensen et al. |
| 2018/0251512 A1 | 9/2018 | Wieczorek et al. |
| 2018/0360918 A1 | 12/2018 | Sauerberg et al. |
| 2019/0231876 A1 | 8/2019 | Pedersen et al. |
| 2019/0314283 A1 | 10/2019 | Vilhelmsen |
| 2020/0000728 A1 | 1/2020 | Pedersen et al. |
| 2020/0079834 A1 | 3/2020 | Wieczorek et al. |

FOREIGN PATENT DOCUMENTS

| | | |
|---|---|---|
| CN | 1867360 A | 11/2006 |
| CN | 101005857 A | 7/2007 |
| CN | 101010339 A | 8/2007 |
| CN | 101133082 A | 2/2008 |
| CN | 101268099 A | 9/2008 |
| CN | 101463081 A | 6/2009 |
| CN | 102946875 A | 2/2013 |
| EP | 0708179 A2 | 4/1996 |
| EP | 0908515 A2 | 4/1999 |
| EP | 1364967 A2 | 11/2003 |
| EP | 2565202 A1 | 3/2013 |
| EP | 2651398 A1 | 10/2013 |
| JP | H05-506427 A | 9/1993 |
| JP | 2004131398 A | 4/2004 |
| JP | 2004521093 | 7/2004 |
| JP | 2006-520818 A | 9/2006 |
| JP | 2007-536268 A | 12/2007 |
| JP | 2008-509933 A | 4/2008 |
| JP | 2009542711 A | 12/2009 |
| JP | 2010-530962 A | 9/2010 |
| JP | 4585037 B2 | 11/2010 |
| JP | 2011509077 A | 3/2011 |
| JP | 2012-121923 A | 6/2012 |
| JP | 2013543814 A | 12/2013 |
| JP | 2014503526 A | 2/2014 |
| JP | 2015-515459 A | 5/2015 |
| KR | 20060100428 A | 9/2006 |
| KR | 102072202 | 1/2020 |
| NZ | 219575 A | 4/1990 |
| RU | 2158138 C2 | 10/2000 |
| RU | 2275207 C2 | 4/2006 |
| WO | 91/11457 | 8/1991 |
| WO | 9111457 A1 | 8/1991 |
| WO | 9614854 A1 | 5/1996 |
| WO | 96/29342 | 9/1996 |
| WO | 9725064 A1 | 7/1997 |
| WO | 9808871 A1 | 3/1998 |
| WO | 98/20895 | 5/1998 |
| WO | 9820885 A1 | 5/1998 |
| WO | 9820895 A1 | 5/1998 |
| WO | 99/43705 A1 | 9/1999 |
| WO | 99/43706 A1 | 9/1999 |
| WO | 99/43707 A1 | 9/1999 |
| WO | 99/43708 A1 | 9/1999 |
| WO | 9964060 | 12/1999 |
| WO | 9964394 A1 | 12/1999 |
| WO | 00/07617 A1 | 2/2000 |
| WO | 00/16797 A2 | 3/2000 |
| WO | 00/34331 | 6/2000 |
| WO | 200048589 A1 | 8/2000 |
| WO | 200050012 A1 | 8/2000 |
| WO | 00/69911 | 11/2000 |
| WO | 0066629 A1 | 11/2000 |
| WO | 01/04156 | 1/2001 |
| WO | 0124777 A1 | 4/2001 |
| WO | 200141737 A2 | 6/2001 |
| WO | 02/46227 A2 | 6/2002 |
| WO | 02/47716 | 6/2002 |
| WO | 0248192 A2 | 6/2002 |
| WO | 03/002158 A1 | 1/2003 |
| WO | 2003005944 A1 | 1/2003 |
| WO | 03/011892 A2 | 2/2003 |
| WO | 03063838 A1 | 8/2003 |
| WO | 03/072195 A2 | 9/2003 |
| WO | 2004/067548 A2 | 8/2004 |
| WO | 04066966 A2 | 8/2004 |
| WO | 2004093823 A2 | 11/2004 |
| WO | 2004/104018 A2 | 12/2004 |
| WO | 2005/005667 A2 | 1/2005 |
| WO | 2005004900 A1 | 1/2005 |
| WO | 2005/014035 A2 | 2/2005 |
| WO | 2005014049 A2 | 2/2005 |
| WO | 2005/027978 A2 | 3/2005 |
| WO | 2005/028516 A2 | 3/2005 |
| WO | 2005/058954 A1 | 6/2005 |
| WO | 2005/058958 A2 | 6/2005 |
| WO | 2005049061 A2 | 6/2005 |

(56) References Cited

FOREIGN PATENT DOCUMENTS

| | | |
|---|---|---|
| WO | 2005/077072 A2 | 8/2005 |
| WO | 2005/077094 A2 | 8/2005 |
| WO | 2005/089786 A2 | 9/2005 |
| WO | 2005/089789 A2 | 9/2005 |
| WO | 2005/089790 A2 | 9/2005 |
| WO | 2005099672 A1 | 10/2005 |
| WO | 2005107462 A2 | 11/2005 |
| WO | 2005107773 A2 | 11/2005 |
| WO | 2005/117984 A2 | 12/2005 |
| WO | 2005/121090 A1 | 12/2005 |
| WO | 2006/005667 A2 | 1/2006 |
| WO | 2006/017251 A2 | 2/2006 |
| WO | 06020207 A2 | 2/2006 |
| WO | 2006/037810 | 4/2006 |
| WO | 06/049681 A2 | 5/2006 |
| WO | 2006/077035 A1 | 7/2006 |
| WO | 2006/082204 A1 | 8/2006 |
| WO | 2006084164 A2 | 8/2006 |
| WO | 2006/097535 A2 | 9/2006 |
| WO | 2006/097536 A2 | 9/2006 |
| WO | 2006/097538 | 9/2006 |
| WO | 2006/097538 A1 | 9/2006 |
| WO | 2006096515 A2 | 9/2006 |
| WO | 2006097537 A2 | 9/2006 |
| WO | 2006103661 A2 | 10/2006 |
| WO | 2006/127948 A2 | 11/2006 |
| WO | 2006124047 A2 | 11/2006 |
| WO | 2006124047 A3 | 11/2006 |
| WO | 2007/009894 A2 | 1/2007 |
| WO | 2007008778 A2 | 1/2007 |
| WO | 2007011958 A2 | 1/2007 |
| WO | 2007024700 A2 | 3/2007 |
| WO | 2007/038943 A1 | 4/2007 |
| WO | 2007038942 A1 | 4/2007 |
| WO | 2007061434 A2 | 5/2007 |
| WO | 2007/068718 A1 | 6/2007 |
| WO | 07065808 A2 | 6/2007 |
| WO | 2007067964 A2 | 6/2007 |
| WO | 2007093226 A1 | 8/2007 |
| WO | 07109354 A2 | 9/2007 |
| WO | 2007117706 A2 | 10/2007 |
| WO | 2007121318 A2 | 10/2007 |
| WO | 2007/128817 A2 | 11/2007 |
| WO | 2007146234 A2 | 12/2007 |
| WO | 2008/003947 A1 | 1/2008 |
| WO | 2008003050 A2 | 1/2008 |
| WO | 2008020096 A1 | 2/2008 |
| WO | 2008028859 A1 | 3/2008 |
| WO | 2008033888 A2 | 3/2008 |
| WO | 2008039351 A2 | 4/2008 |
| WO | 08/053360 A2 | 5/2008 |
| WO | 2008/087186 A2 | 7/2008 |
| WO | 2008/087190 A2 | 7/2008 |
| WO | 2008109385 A2 | 9/2008 |
| WO | 2008132435 A1 | 11/2008 |
| WO | 2008/154619 A1 | 12/2008 |
| WO | 2009007714 A2 | 1/2009 |
| WO | 2009/030771 A1 | 3/2009 |
| WO | 2009030738 A1 | 3/2009 |
| WO | 2009032749 A2 | 3/2009 |
| WO | 2009033710 A1 | 3/2009 |
| WO | 2009/050738 A2 | 4/2009 |
| WO | 09042922 | 4/2009 |
| WO | 09042922 A2 | 4/2009 |
| WO | 2009059188 A1 | 5/2009 |
| WO | 2009/083549 A1 | 7/2009 |
| WO | 2009/138511 A1 | 11/2009 |
| WO | 2010020978 A1 | 2/2010 |
| WO | 2010/029159 A1 | 3/2010 |
| WO | 10031707 A1 | 3/2010 |
| WO | 2010031521 A2 | 3/2010 |
| WO | 2010/043319 A1 | 4/2010 |
| WO | 2010052144 A2 | 5/2010 |
| WO | 2010/092163 A2 | 8/2010 |
| WO | 2010096175 A1 | 8/2010 |
| WO | 2011/029551 A2 | 3/2011 |
| WO | 11033068 A1 | 3/2011 |
| WO | 2011033068 A1 | 3/2011 |
| WO | 11045232 A2 | 4/2011 |
| WO | 2011058165 A1 | 5/2011 |
| WO | 2011084618 A2 | 7/2011 |
| WO | 2011094531 A1 | 8/2011 |
| WO | 2011109787 A1 | 9/2011 |
| WO | 2011116139 A2 | 9/2011 |
| WO | 2011131646 A1 | 10/2011 |
| WO | 2011138421 A1 | 11/2011 |
| WO | 2012080471 A1 | 6/2012 |
| WO | 2012140117 A1 | 10/2012 |
| WO | 2013009545 A1 | 1/2013 |
| WO | 2013139694 A1 | 9/2013 |
| WO | 2013139695 A1 | 9/2013 |
| WO | 2013189988 A1 | 12/2013 |
| WO | 2014005858 A1 | 1/2014 |
| WO | 2014177683 A1 | 11/2014 |
| WO | 2014178018 A1 | 11/2014 |
| WO | 2015071355 A1 | 5/2015 |
| WO | 2016128970 A1 | 8/2016 |
| WO | 2016128971 A1 | 8/2016 |
| WO | 2016128972 A1 | 8/2016 |
| WO | 2016128973 A1 | 8/2016 |
| WO | 2016128974 A1 | 8/2016 |
| WO | 2016198682 A1 | 12/2016 |
| WO | 2017060500 A1 | 4/2017 |

OTHER PUBLICATIONS

Physicians' Desk Reference, 54th Edition, 2000, p. 1291.
Physicians' Desk Reference, 63rd Edition, 2009, p. 1638.
Arbit et al. "Oral heparin: status review". Thrombosis J, May 2006, vol. 4, No. 6, pp. 1-7.
Emisphere Announces License Agreement With Novo Nordisk to Develop Oral Formulation of GLP-1 Receptor Agonists for Diabetes, Jun. 23, 2008 retrieved from https://www.biospace.com/article/releases/emisphere-technologies-inc-announces-license-agreement-with-novo-nordisk-inc-to-develop-oral-formulation-of-glp-1-receptor-agonists-for-diabetes-/, 5 pages, retrieved on Dec. 16, 2020.
European Medicines Agency, Rybelsus EPAR Public Assessment Report, Jan. 30, 2020, pp. 1-152, p. 72.
Notice of Opposition by Galenicum, filed Dec. 9, 2020 in European Patent 3326620.
Notice of Opposition by Hexal Ag, filed Dec. 8, 2020 in European Patent 3326620.
Novo Nordisk starts phase 1 trial with long-acting oral GLP-1 analogue, Jan. 13, 2010, 2 pages retrieved from https://pipelinereview.com/index.php/2010011332046/Small-Molecules/Novo-Nordisk-starts-phase-1-trial-with-long-acting-oral-GLP-1-analogue.html, retrieved on Dec. 16, 2020.
Novo Nordisk, "Novo Nordisk to acquire Emisphere Technologies and obtain ownership of the Eligen® SNAC oral delivery technology", Nov. 6, 2020 retrieved from <https://www.novonordisk.com/content/nncorp/global/en/news-and-media/news-and-ir-materials/news-details.html?id=33374>, 3 pages retrieved on Dec. 16, 2020.
Notice of Opposition by Teva filed Dec. 4, 2020 in European Patent 3326620.
U.S. Appl. No. 61/425,087 P (priority of opposed patent), filed Dec. 20, 2010.
Application No. 10195285.1 (priority of opposed patent), Dec. 16, 2010.
Steinert et al., 2010, Am J Clin Nutr, vol. 92, pp. 810-817.
Nauck et al., 2012, Abstracts of the 48th European Association for the Study of Diabetes Annual Meeting of the EASD, Oct. 1-5, 2012, Berlin, Germany, Diabetologia, 2012, vol. 55, Suppl, S7.
Maher Sam et al., Overcoming poor permeability: translating permeation enhancers for oral peptide delivery, Journal: Drug Discovery Today:Technologies, Year: 2011, vol. 9, No. 2, pp. e113-e119.
Maher Sam et al., Safety and efficacy of sodium caprate in promoting oral drug absorption: from in vitro to the clinic, Journal: Advanced Drug Delivery Reviews, Year: 2009, vol. 61, pp. 1427-1449.

(56) References Cited

OTHER PUBLICATIONS

Michel Marre et al., GLP-1 receptor agonists today, Journal: Diabetes Research; and Clinical Practice, Year: 2011, vol. 93, No. 3, pp. 317-327.
Walsch Edwin G et al., Oral delivery of macromolecules: rationale underpinning Gastrointestinal Permeation Enhancement Technology (GIPET®), Journal: Therapeutic Delivery, Year: 2011, vol. 2, No. 12, pp. 1595-1610. OTH.
Makoto Otsuka, Chemoinformetrical evaluation of granule and tablet properties of pharmaceutical preparations by near-infrared spectroscopy, "Chemometrics and Intelligent Laboratory Systems" Year 2006, vol. 82, No. 1-2, pp. 109-114.
Shah R. B et al. Process Analytical Technology: Chemometric Analysis of Raman and Near Infra-red Spectroscopic Data for Predicting Physical Properties of Extended Release Matrix Tablets, "Journal of Pharmaceutical Sciences" Year 2007, vol. 96, No. 5, pp. 1356-1365.
Aenugu H.P.R et al. Near Infra Red Spectroscopy—An Overview, "International Journal of ChemTech Research" Year 2011, vol. 3, No. 2, pp. 825-836.
Donoso M et al. Prediction of Tablet Hardness and Porosity Using Near-Infrared Diffuse Reflectance Spectroscopy as a Nondestructive Method, "Pharmaceutical Development and Technology" Year 2003, vol. 8, No. 4, pp. 357-366.
Jeckel et al. Importance of particle size knowledge for tablet porosity determination by NIRS, "Tablet Tech Seminar, FMC Biopolymer" Year 2007, retrieved from the Internet: URL:http://www.pharmtech.uni-bonn.de/forschung/arbeitskreis-porf-steffens/download-16, the whole document.
Remington, The Science and Practice of Pharmacy, 22nd Edition, 2012.
Felix Kratz "A Clinical Update of Using Albumin as a Drug Vehicle—A Commentary" Journal of Controlled Release 2014 vol. 190 pp. 331-336.
Rivera et al. Oral Delivery of Heparin in Combination with Sodium N-[8-(2-Hydroxybenzoyl)amino]caprylate: Pharmacological Considerations. Pharmaceutical Research 1997 vol. 14 No. 12 pp. 1830-1834.
Su Young Chae et al. "Preparation, Characterization and Application of Biotinylated and Biotin-PEGylated Glucagon-Like Peptide-1 Analogues for Enhanced Oral Delivery." Bioconjugate Chemistry 2008 vol. 19 No. 1 pp. 334-341.
Emisphere Technologies. "Carriers Enhance Drug Delivery" Manufacturing Chemistry 1999 vol. 70 No. 6 pp. 25-26.
Adam W. G. Alani et al., "Mechanistic Understanding of Oral Drug Absorption Enhancement of Cromolyn Sodium by an Amino Acid Derivative," Pharmaceutical Research, 2008, vol. 25, No. 1, pp. 48-54.
Bhansali et al., "Historical Overview of Incretin Based Therapies," Supplement to JAPI, 2010, vol. 58, pp. 10-14.
Valentino et al., "Central and Peripheral Molecular Targets for Antiobesity Pharmacotherapy," Clinical Pharmacology and Therapeutics, 2010, vol. 87, No. 6, pp. 652-662.
Bastin et al., "Salt Selection and Optimisation Procedures for Pharmaceutical New Chemical Entities," Org Proc Res & Devt, 2000, vol. 4, pp. 427-435.
Drug Data Report, 2006, vol. 28, p. 933.
Anonymous, "Eligen@ Technology. Summary and Value Proposition", Emisphere, Feb. 24, 2017, pp. 1-10, URL: https://www.emisphere.com/wp-content/uploads/2017/02/Eligen-Technology-Presentation_2.15-Update.pdf, XP055520567.
Keck et al., Moderne Pharmazeutische Technologie, 2009, pp. 8-14.
Kidron et al., "A Novel Per-Oral Insulin Formulation: Proof of Concept Study in Non-Diabetic Subjects," Diabetic Medicine, 2004, vol. 21, pp. 354-357.
Letter to Sandoz International GmbH regarding English translation of claim of patent JP4585037, dated Aug. 29, 2018.
Mullins, "Statistics for the Quality Control Chemistry Laboratory," 2003, Chapter I, pp. 10-17.
SNAC, Synchem, http://www.synchem.de/product/snac, accessed Aug. 16, 2018.
Valentino et al., "Current Trends in Targeting the Hormonal Regulation of Appetite and Energy Balance to Treat Obesity," Expert Rev Endocrinol Metab, 2010, vol. 5, pp. 765-783.
WHO Drug Information, "International Nonproprietary Names for Pharmaceutical Substances," 2009, vol. 23, No. 2, p. 164.
U.S. Appl. No. 61/425,087, filed Dec. 20, 2010.
EP Application No. 10195285.1, filed Dec. 16, 2010.
Wang et al., "Non-peptidic glucose-like peptide-1 receptor agonists: aftermath of serendipitous discovery," Acta Pharmacol. Sinica, 2010, vol. 31, pp. 1026-1030.
Baynes, Kevin C. R., "The evolving world of GLP-1 agonist therapies for type 2 diabetes" Therapeutic Advances in Endocrinology and Metabolism, 2010,,vol. 1, No. 2, pp. 61-67.
Buckley, Stephen T. et al., "Transcellular stomach absorption of a derivatized glucagon-like peptide-1 receptor agonist" Science Translational Medicine, Nov. 14, 2018, vol. 10, pp. 1-14.
Christensen, Mikkel et al., "Once-Weekly GLP-1 Agonists: How Do They Differ from Exenatide and Liraglutide?" Curr Diab Rep, 2010, vol. 10, pp. 124-132.
Davies, Melanie et al., "Effect of Oral Semaglutide Compared with Placebo and Subcutaneous Semaglutide on Glycemic Control in Patients with Type 2 Diabetes" JAMA, 2017, vol. 318, pp. 1460-1470.
Declaration by the Inventor, Flemming S. Nielsen, dated Feb. 11, 2019.
EMEA Assessment Report EMEA/379172/2009 for Victoza (liraglutide), 2009.
Goldberg, Michael et al., "Challenges for the Oral Delivery of Macromolecules" Nature Reviews Drug Discovery, 2003, vol. 2, pp. 289-294.
Granhall, Charlotte et al., "Safety and Pharmacokinetics of Single and Multiple Ascending Doses of the Novel Oral Human GLP-1 Analogue, Oral Semaglutide, in Healthy Subjects and Subjects with Type 2 Diabetes" Clinical Pharmacokinetics, published Dec. 18, 2018.
Hellriegel, Edward T. et al., "Interpatient variability in bioavailability is related to the extent of absorption: Implications for bioavailability and bioequivalence studies" Clinical Pharmacology & Therapeutics, Dec. 1996, vol. 60, No. 6, pp. 601-607.
King, Simon, "ViewPoints: Novo Nordisk R&D chief predicts an oral revolution for biologics" Nov. 14, 2018, Available from: [http://www.firstwordpharma.com/print/1604592?tsid=17].
Lee, Hye J., "Protein Drug Oral Delivery: The Recent Progress" Archives of Pharmacal Research, 2002, vol. 25, No. 5, pp. 572-584.
Madsen, Kjeld et al., "Structure—Activity and Protraction Relationship of Long-Acting Glucagon-like Peptide-1 Derivatives: Importance of Fatty Acid Lenght, Polarity, and Bulkiness" J. Med. Chem., 2007, vol. 50, pp. 6126-6132.
Morishita, Mariko et al., "Is the oral route possible for peptide and protein drug delivery?" Drug Discovery Today, Oct. 2006, vol. 11, No. 19/20, pp. 905-910.
Novo Nordisk Company announcement No. 14/2015, Novo Nordisk announces positive results for phase 2 trial with oral semaglutide in people with type 2 diabetes, www.novonordisk.com CVR No. 24256790, dated Feb. 20, 2015, p. 1-2.
Novo Nordisk Company announcement No. 52/2015, Novo Nordisk to initiate phase 3a development of oral semaglutide, a once-daily oral GLP-1 analogue, www.novonordisk.com CVR No. 24256790, dated Aug. 26, 2015, p. 1-2.
Novo Nordisk Company announcement No. 17/2018, Novo Nordisk successfully completes the first phase 3a trial, Pioneer 1, with oral semaglutide, www.novonordisk.com CVR No. 24256790, dated Feb. 22, 2018, p. 1-3.
Novo Nordisk Company announcement No. 47/2018, Oral semaglutide shows superior improvement in HbA1C vs empagliflozin in the Pioneer 2 trial, www.novonordisk.com CVR No. 24256790, dated May 29, 2018, p. 1-3.
Novo Nordisk Company announcement No. 51/2018, Oral semaglutide shows statiistically significantly greater reductions in HbA1c and

(56) References Cited

OTHER PUBLICATIONS weight compared to Victoza® and sitagliptin in the Pioneer 4 and 7 trials, www.novonordisk.com CVR No. 24256790, dated Jun. 20, 2018, p. 1-4.

Study NCT02014259, version 1, published Dec. 18, 2013, accessed Jun. 5, 2019.

"Drug Absorption, Distribution and Elimination; Pharmacokinetics" http://www.columbia.edu/itc/gsas/g9600/2004/GrazianoReadings/Drugabs.pdf, available since at least Apr. 24, 2006, accessed on Jun. 3, 2019.

"Standards of Medical Care in Diabetes—2010", Diabetes Care, vol. 33, supplement 1, Jan. 2010, pp. S11-S61.

Andrew D. Morris, MD, "Addressing dosing frequency in diabetes: a simple approach to improving adherence to therapy and clinical outcomes," The Diabetes Educator, 2003, vol. 29, No. 3, pp. 440-453.

B.J. Aungst, "Absorption Enhancers: Applications and Advances," The AAPS Journal, 2012, vol. 14, No. 1, pp. 10-18.

ClinicalTrials.gov archive: History of Changes for Study NCT01686945, trackchange of version of Apr. 15, 2013 (published Apr. 16, 2013) as compared to version of Sep. 13, 2012 (published Sep. 18, 2012). Clinicaltrials.gov, NCT01686945, page as viewed in Apr. 2013, https://clinicaltrials.gov/ct2/history/NCT01686945?A=5&B=5&C=merged#StudyPageTop.

Coskun et al., "LY3298176, a novel dual GIP and GLP-1 receptor agonist for the treatment of type 2 diabetes mellitus: From discovery to clinical proof of concept," Molecular Metabolism, 2018, vol. 18, pp. 3-14.

David J. Edmonds et al., "Oral GLP-1 Modulators for the Treatment of Diabetes". Annual Reports in Medicinal Chemistry, 2013, 1st edition, vol. 48, Chapter 9, pp. 119-130.

DJ. Birkett, "Pharmacokinetics made easy 11 Designing dose regimens," Australian Prescriber, 1996, vol. 19, No. 3, pp. 76-88.

E. Mutschler et al., Mutschler Arzneimittelwirkungen, Lehrbuch der Pharmakologie und Toxikologie, 8th edition 2001, pp. 48-51.

Emisphere Annual Report and Proxy 2013, publicly available at the latest on Apr. 17, 2014.

EU Clinical Trials Register Summary EudraCT No. 2012-004994-16 (NN9924-3790), published Jul. 30, 2013, accessed Jun. 7, 2019.

EU Leaflet of Linagliptin, 1st authorization in EU: Aug. 24, 2011 (p. 2, 3 & 13).

EU Leaflet of Linagliptin-Metformin, 1st authorization in EU:Jul. 20, 2012 (p. 2, 3 & 21).

EU Leaflet of Metformin, 1st authorization in EU: Jul. 31, 2001 (p. 1, 2 & 11).

EU Leaflet of Saxagliptin, 1st authorization in EU: Oct. 1, 2009 (p. 1 & 18).

EU Leaflet of Sitagliptin, 1st authorization in EU: Mar. 21, 2007 (p. 2, 3 & 16).

EU Leaflet of Sitagliptin-Metformin, 1st authorization in EU: Jul. 16, 2008 (p. 2, 3 & 20).

EU Leaflet of Vildagliptin, 1st authorization in EU: Sep. 26, 2007(p. 2, 3 & 18).

EU Leaflet of Vildagliptin-Metformin, 1st authorization in EU: Nov. 14, 2007 (p. 2, 3 & 21).

European Patent Application 13166205, filed May 2, 2013.

Geiser et al., "Clinical Pharmacokinetics of Dulaglutide in Patients with Type 2 Diabetes: Analyses of Data from Clinical Trials". Clinical Pharmacokinetics, 2016, vol. 55, pp. 625-634.

Granhall et al, Safety and Pharmacokinetics of Single and Multiple Ascending Doses of the Novel Oral Human GLP-1 Analogue, Oral Semaglutide, in Healthy Subjects and Subjects with Type 2 Diabetes, Clinical Pharmacokinetics, Dec. 2018.

Leon Shargel, Applied Biopharmaceutics and Pharmacokinetics, 6th edition, 2012, Chapter 8, Multiple-Dosage Regimens, pp. 153-175.

Linda Felton, Remington, Essentials of Pharmaceutics, 2012, Chapter 37, pp. 708-709 and 712-713.

M. Gonzalez Brao, "48th Annual Meeting of the European Association for the Study of Diabetes (EASD)," Drugs of the Future, 2012, vol. 37, No. 12, pp. 871-878.

Malcolm Rowland et al., "Clinical Pharmacokinetics and Pharmacodynamics : Concepts and Applications," Chapter 11—Multiple-Dose Regimens (pp. 293-329); 4th ed.; Philadelphia: Wolters Kluwer Health/Lippincott William & Wilkins, 2011.

Product details regarding David J. Edmonds et al., "Oral GLP-1 Modulators for the Treatment of Diabetes". Annual Reports in Medicinal Chemistry (2013), 1st edition, vol. 48, chapter 9, pp. 119-130, from amazon.com, accessed on May 3, 2019.

Prosecution file of EP2991671B1, available at the EPO Register, the pdf is not attached. https://register.epo.org/application?number=EP14721834&lng=en&tab=doclist, accessed Jun. 14, 2019.

Quianzon et al., "Lixisenatide-Once daily glucagon-like peptide-1 receptor agonist in the management of type 2 diabetes," 2011, US Endocrinology, Diabetes Management, vol. 7, No. 2, pp. 104-109.

Rosenstock et al., "Potential of albiglutide, a long-acting GLP-1 receptor agonist, in type 2 diabetes: a randomized controlled trial exploring weekly, biweekly, and monthly dosing". Diabetes Care, 2009, vol. 32, No. 10, pp. 1880-1886.

S. Dhillon et al., "Basic Pharmacokinetics," Clinical Pharmacokinetics, 2006, Pharmaceutical Press, London; Chapter 1, pp. 1-44.

Sarfaraz K. Niazi, Handbook of Bioequivalence Testing, 2007, p. 13-15.

Sisson, "Liraglutide: clinical pharmacology and considerations for therapy," Pharmacotherapy, 2011, vol. 31, pp. 896-911.

Study NCT01686945, version 1, published Sep. 18, 2012, accessed Jun. 6, 2019.

Study NCT01866748, version 1, published May 31, 2013, accessed Jun. 6, 2019.

Study NCT01923181, version 1, published Aug. 15, 2013, accessed Jun. 5, 2019.

Submission of Novo Nordisk dated Feb. 15, 2019 in response to oppositions against EP2651398B1.

He Xiaorong et al., Mechanistic Study of the Effect of Roller Compaction and Lubricant on Tablet Mechanical Strength, Journal: Journal of Pharmaceutical Sciences,Year: 2007, vol. 96, No. 5, pp. 1342-1355.

Mollan Jr. Matthew J. et al., The effects of lubrication on the compaction and post-compaction properties of directly compressible maltodextrins, Journal: International Journal of Pharmaceutics, Year: 1996, vol. 144, Issue 1, pp. 1-9.

Rowe Raymond C et al., Book: Handbook of Pharmaceutical Excipients, Title: Acesulfame Potassium, Edition—5th, Year: 2006, Complete book.

Steinert R E et al., Orally Administered Glucagon-Like Peptide-1 Affects Glucose Homeostasis Following an Oral Glucose Tolerance Test in Healthy Male Subjects, Journal: Clinical Pharmacology and Therapeutics, Year: 2009, vol. 86, No. 6, pp. 644-650.

Von Eggelkraut-Gottanka Stephan G. et al., Roller Compaction and Tabletting of St. John's Wort Plant Dry Extract Using a Gap Width and Force Controlled Roller; Compactor. II. Study of Roller Compaction Variables on Granule and Tablet Properties by a 33 Factorial Design, Journal: Pharmaceutical Development and Technology, Year: 2002, vol. 7, No. 4, pp. 447-455.

Beglinger C et al., Clinical Pharmacology and Therapeutics,"Pharmacokinetics and Pharmacodynamic Effects of Oral GLP-1 and PYY3-36: A Proof-of-Concept Study in Healthy Subjects"., 2008, vol. 84, No. 4, pp. 468-474.

Steinert RE et al, American Journal of Clinical Nutrition,"Oral Administration of Glucagon-Like Peptide 1 or Peptide YY 3-36 Affects Food Intake in Healthy Male Subjects", 2010, vol. 92, pp. 810-817.

Beglinger C et al., Pharmacokinetics and Pharmacodynamic Effects of Oral GLP-1 and PYY3-36: A Proof-of-concept Study in Healthy Subjects, Journal: Clinical Pharmacology & Therapeutics, Nature Publishing Group, Year: 2008. vol. 84, No. 4, pp. 468-474.

Leonard Thomas W et al., Promoting absorption of drugs in humans using medium-chain fatty acid-based solid dosage forms:GIPET™, Journal: Expert Opinion Drug Delivery, Year: 2006, vol. 3(5), pp. 685-692.

File History of European Patent 2827845, filed Mar. 15, 2013.

(56) References Cited

OTHER PUBLICATIONS

File History of U.S. Appl. No. 61/662,456, filed Jun. 21, 2012.
Handbook of Pharmaceutical Excipients, 6th Edition, 2009, pp. 404-407 and 651-653.
History of changes for clinical trial NCT01037582, from Mar. 17, 2011, https://clinicaltrials.gov/ct2/history/NCT01037582?A=5&C=merged#StudyPageTop.
Kikuta et al., "Effect of Mixing Time on the Lubricating Properties of Magnesium Stearate and the Final Characteristics of the Compressed Tablets," Drug Development and Industrial Pharmacy, 1994, vol. 20, No. 3, pp. 343-355.
Lieberman et al., Pharmaceutical Dosage Forms: Tablets, 2nd Edition, 1989, Chapter 5, pp. 247-284.
Parikh, Handbook of Pharmaceutical Granulation Technology, 3rd Edition, 2010, Informa Healthcare, pp. 2-3.
Remington, The Science and Practice of Pharmacy, 21st Edition, 2005, Lippincott, Williams & Wilkins, pp. 677, 892-893, 896, and 1040.
Summary of Product Characteristics for Valtrex 500mg Tablets, 2019.
Teng et al., "Systematical approach of formulation and process development using roller compaction," European Journal of Pharmaceutics and Biopharmaceutics, 2009, vol. 73, pp. 219-229.
The Handbook of Pharmaceutical Granulation Technology, Chapters 2, 8, and 9, 2010.
Uros Markoja, Semaglutide-Experiment report for opposition against EP2827845B1, dated Sep. 24, 2019, pp. 1-6.
Valtrex prescribing information, Oct. 2007.
Venables et al., "Powder Mixing," Drug Development and Industrial Pharmacy, 2001, vol. 27, No. 7, pp. 599-612.
Tyagi et al., "Oral peptide delivery: Translational challenges due to physiological effects," J. Controlled Release, 2018, vol. 287, pp. 167-176.
Dahlgren et al., "Intestinal absorption-modifying excipients: A current update on preclinical in vivo evaluations," European J. of Pharm. and Biopharmaceutics, 2019, vol. 142, pp. 411-420.
Figures presenting plasma concentration, described in EU Patent No. 2991671, issued Aug. 15, 2018.
FDA News Release, "FDA approved first oral GLP-1 treatment for type 2 diabetes," Sep. 20, 2019.
Carly Helfand, "Novo Nordisk wins FDA green light for "holy grail" diabetes drug Rybelsus," Fierce Pharma, Sep. 20, 2019, https://www.fiercepharma.com/pharma/novo-nordisk-wins-fda-green-light-for-holy-grail-oral-semaglutide, accessed Oct. 4, 2019.
Full European prosecution file of EP 2 827 885 BI. Published Jan. 28, 2015, Available at the EPO Register, https://register.epo.org/application?number=EP13709231&lng=en&tab=doclist, accessed May 31, 2019.
Post-published details of trial NCT01037582. First posted Dec. 23, 2009 https://clinicaltrials.gov/ct2/show/NCT01037582, accessed May 31, 2019.
Published details of trial NCT01037582 First Version Dec. 21, 2009 https://clinicaltrials.gov/ct2/history/NCT01037582?A=1&B=1&C=merged#StudyPageTop, accessed May 31, 2019.
Table summarizing the components of the tablet compositions B to F, described in EP Patent No. 2827885, issued Aug. 15, 2018.
Schematic drawing of tablets E and F described in EP Patent No. 2827885, issued Aug. 15, 2018.
Overview of claim 1 of the main and auxiliary requests, European Application No. EP2651398, filed May 14, 2013.
Banakar et al, Critical Considerations in Pharmaceutical Bioequivalence Testing, Journal of Pharmacy of University of Marmara, 1995, vol. 11 Nos. 1-2, pp. 55-80.
Emisphere Technologies, Inc., Form 10-K, 2013 Annual Report, Published Mar. 31, 2014.
American Veterinary Medical Association, "The Veterinarian-Client-Patient Relationship (VCPR)," https://www.avma.org/policies/veterinarian-client-patient-relationship, accessed Mar. 11, 2020.
Novo Nordisk Company announcement No. 53/2018, Oral semaglutide shows superior reductions in HbA1c and weight compared to sitagliptin in the long-term safety and efficacy trial, Pioneer 3, www.novonordisk.com CVR No. 24256790, dated Jun. 28, 2018, p. 1-3.
Novo Nordisk Company announcement No. 66/2018, Oral semaglutide provides superior HbA1c and weight reductions versus placebo in people with type 2 diabetes and renal impairment in the Pioneer 5 trial, www.novonordisk.com CVR No. 24256790, dated Aug. 20, 2018, p. 1-3.
Novo Nordisk Company announcement No. 74/2018, Oral semaglutide demonstrates greater reductions in HbA1c and body weight and comparable number of adverse events vs dulaglutide in Japanese people with type 2 diabetes, www.novonordisk.com CVR No. 24256790, dated Sep. 20, 2018, p. 1-3.
Novo Nordisk Company announcement No. 81/2018, Oral semaglutide demonstrates statistically significant reductions in HbA1c and body weight in people with long duration of type 2 diabetes treated with insulin, www.novonordisk.com CVR No. 24256790, dated Oct. 26, 2018, p. 1-3.
Novo Nordisk Company announcement No. 89/2018, Oral semaglutide demonstrates greater reductions in both HbA1c and body weight compared to Victoza® in Japanese people with type 2 diabetes, www.novonordisk.com CVR No. 24256790, dated Nov. 22, 2018, p. 1-2.
Novo Nordisk Company announcement No. 90/2018, Oral semaglutide demonstrates a favourable cardiovascular safety profile and a significant reduction in cardiovascular death and all-casue mortality in people with type 2 diabetes in the Pioneer 6 trial, www.novonordisk.com CVR No. 24256790, dated Nov. 23, 2018, p. 1-3.
Owens, D.R. et al., "Alternative routes of insulin delivery" Diabetic Medicine, 2003, vol. 20, pp. 886-898.
Thepharmaletter, "'8-10 years ahead' of field in oral delivery, senior execs say Novo is becoming a GLP-1 company" May 16, 2018, [cited Jan. 24, 2019] Available from: [https://www.thepharmaletter.com/article/8-10-years-ahead-of-field-in-oral-delivery-senior-execs-say-novo-nordisk-is-becoming-a-glp-1-company].
Watson, Estelle et al., "Population Pharmacokinetics of Liraglutide, a Once-Daily Human Glucagon-Like Peptide-1 Analog, in Healthy Volunteers and Subjects With Type 2 Diabetes, and Comparison to Twice-Daily Exenatide" J. Clin Pharmacology, 2010, vol. 50, pp. 886-894.
Antony J Hickey et al., Pharmaceutical Process Engineering (Second edition) (2010) p. 155-168.
Bruce J. Aungst, "Absorption enhancers: applications and advances," The MPS Journal, 2011, vol. 14, No. 1, pp. 10-18.
Diabetes Close Up, Baby Steps, Mar./Apr. 2011, No. 106, pp. 1-50.
Dilip M. Parikh, Handbook of Pharmaceutical Granulation Technology (Second edition) (2005), Process-related variables, pp. 7-19 and 311-331.
EP Application 12160743, filed Mar. 22, 2012.
EP Application 13153459, filed Jan. 31, 2013.
Full European prosecution file of EP 2 827 885 BI. Available at the EPO Register, https://register.epo.org/application?number=EP13709231&lng=en&tab=doclist, accessed May 31, 2019.
Dilip M Parikh, Handbook of Pharmaceutical Granulation Technology, Drugs and pharmaceutical sciences, Second Edition, 2005, vol. 154, Introduction, pp. 1-6.
Post-published details of trial NCT01037582 https://clinicaltrials.gov/ct2/show/NCT01037582, accessed May 31, 2019.
Published details of trial NCT01037582 (Dec. 2009) https://clinicaltrials.gov/ct2/history/NCT01037582?A=1&B=1&C=merged#StudyPageTop, accessed May 31, 2019.
R. F. Witkamp, "Current and Future Drug Targets in Weight Management," Pharm Res, 2011, vol. 28, pp. 1792-1818.
Salem et al., "Approaches to the pharmacological treatment of obesity," Expert Rev Clin Pharmacol, 2010, vol. 3, No. 1, pp. 73-88.
Barrera-Medrano et al., The Handbook of Powder Technology "Granulation", Chp. 25 granule structure, vol. 11, 2007, p. 1189-1212.
U.S. Appl. No. 61/748,840, filed Jan. 4, 2013.
Melanie Davies et al., "Effect of Oral Semaglutide Compared With Placebo and Subcutaneous Semaglutide on Glycemic Control in

(56) References Cited

OTHER PUBLICATIONS

Patients With Type 2 Diabetes: A Randomized Clinical Trial," JAMA the Journal of the American Medical Association, 2017, vol. 318, No. 15, p. 1460.
Steinert et al., "Oral Administration of Glucagon-Like Peptide 1 or Peptide YY 3-36 Affects Food Intake in Healthy Male Subjects," Am J Clin Nutr, Oct. 2010, vol. 92, No. 4, pp. 810-817.
Chae S Y et al., Journal Title: Journal of the Controlled Release,Title: The Fatty Acid Conjugated Exendin-4 Analogs for Type 2 Antidiabetic Therapeutics ,Year: 2010,vol. 144,pp. 10-16.
Dolensky et al., "New Building Blocks for Fluorinated Imidazole," Jorunal of Organic Chemistry, vol. 66(13), pp. 4687-4691 (2001).
Knudsen et al., "Potent Derivatives of Glucagon-Like Peptide-1 With Pharmacokinetic Properties Suitable for Once Daily Administration," Journal of Medicinal Chemistry, 2000, vol. 43(9), pp. 1664-1669.
Dumelin et al.., "A Portable Albumin Binder From a DNA-Encoded Chemical Library", Angewandte Chemie (International Edition in English), vol. 47(17), pp. 3196-3201 (2008).
Rawlay SS et al. Journal of Organic Chemistry. "Oxidation of Primary, Secondary, and Tertiary Amines With Neutral Permanganate. A Simple Method for Degrading Amines to Aldehydes and Ketones." 1967. vol. 32(10). pp. 3129-3131.
Travis B R et al. Organic Letters. "Facile Oxidation of Aldehydes to Acids and Esters With Oxone." 2003. vol. 5(7). pp. 1031-1034.
Murage E N et al. Bioorganic & Medicinal Chemistry. "Search for ¿-Helical Propensity in the Receptor-Bound Conformation of Glucagon-Like Peptide-1." 2008. vol. 16. pp. 10106-10112.
Runge et al., "Crystal Structure of the Ligand-Bound Glucagon-Like Peptide-1 Receptor Extracellular Domain," J Biol Chem 2008, vol. 283, No. 17, pp. 11340-11347.
Adelhorst, K et al Journal of Biological Chemistry Structure Activity Studies of GLP-1 1994 269 9 6275-6278.
Knudsen, L.B. Journal of Medicinal Chemistry Glucagon-Like Peptide-1: The Basis of a New Class of Treatment for Type 2 Diabetes 2004 47 17 4128-4134.
Leger et al., "Identification of CJC-1131-Albumin Bioconjugate as a Stable and Bioactive GLP-1 (7-36) Analog," Bioorganic and Medicinal Chemistry Letters, vol. 14, pp. 4395-4398 (2004).
Pan, 2006 Journal of Biological Chemistry vol. 281 pp. 12506-12515.
The Medical Dictionary Online. http://cancerweb.ncl.ac.uklomd/about.html. 2005.
Nauck, M A. Regulatory Peptides. "Glucagon-Like Peptide 1 and its Derivatives in the Treatment od Diabetes." 2005. vol. 128(2). pp. 135-148.
David M. Irwin, Trout and chicken Proglucagon: Alternative Splicing Generates mRNA Transcripts Encoding Glucagon-Like Peptide 2, Molecular Endocrinology, 1995, vol. 9 No. 3, 267-277.
"Formulation and Analytical Development for Low-Dose Oral Drug Products," Wiley, 2009, p. 194.
"International Nonproprietary Names for Pharmaceutical Substances (INN)," WHO Drug Information, 2009, vol. 23, No. 2, p. 129.
"Sodium Lauryl Sulfate," Handbook of Pharmaceutical Excipients, 2009, 6th Edition, pp. 651-653.
Ajaz S. Hussain, "A Collaborative Search for Efficient Methods of Ensuring Unchanged Product Quality and Performance During Scale-Up of Immediate-Release Solid Oral Dosage Forms," Pharmaceutical Process Scale-Up, 2002, 1st Edition, Chapter 11, pp. 325-352.
Bai et al., Excipient Development for Pharmaceutical, Biotechnology, and Drug Delivery Systems, 2006, Chapter 12, pp. 181-185.
C. M. Keck et al., "Moderne Pharmazeutische Technologie—Lehbuch fur Studierende," 1. Auflage (2009), Kapitel 1.2 H. J. Ji.inginger, "Delivery Systeme fur die perorale Applikation van Peptiden," pp. 1-14.
European Application No. 12172739.0, filed Jun. 20, 2012.
Fonseca et al., "Efficacy and Safety of the Once-Daily GLP-1 Receptor Agonist Lixisenatide in Monotherapy," Diabetes Care, Jun. 2012, vol. 35, pp. 1225-1231.
ClinicalTrials.gov archive: History of Changes for Study NCT01923181 (NN9924-3790), Jan. 31, 2018, 14 Pages.
Schematic overview of sequences and plasma half-life in humans of "GLP-1 peptides" cited as E4 in Sanofi Opposition in EP2991671, dated May 22, 2019, 1 Page.
Granulation Handbook, Chapter 4. Compression Granulation Method, May 30, 1975, 1st Edition First Press, p. 173-197.
Design and evaluation of formulation for oral administration, Problem arising from industrialization and process scale-up and corresponding solutions, Feb. 10, 1995, p. 264-279.
EP09179390.1 Priority Application Filed on Dec. 16, 2009 by Novo Nordisk. Double-Acylated GLP-1 Derivatives, 100 pages.
EP10190515.6 Priority Application Filed on Nov. 9, 2010 by Novo Nordisk. Double-Acylated GLP-1 Derivatives, 162 pages.
Guohu et al "Progress of Pharmaceutical Studies on Diabetes" Practical Pharmacy and Clinic, 2007, vol. 10, No. 1, pp. 56-57.
Kusher IV et al., "Scale-up model describing the impact of lubrication on tablet tensile strength," International Journal of Pharmaceutics, 2010, vol. 399, Nos. 1-2, pp. 19-30.
Sakr et al., "Oral Solid Dosage Forms," Remington, Essentials of Pharmaceutics, 1st Edition, Chapter 30, 2012, pp. 581-610.
Full prosecution file of the opposed patent EP 3326620 B1, filed on Nov. 29, 2017 that can be found in European Patent register, 1,596 pages, accessed Dec. 3, 2021 https://reqister.epo.orq/application?number=EP17204363&lnQ=en&tab=doclist.
Full prosecution file of the parent patent EP2651398B1, filed May 14, 2013 that can be found in European Patent register, 4309 pages, accessed Dec. 3, 2021, https://register.epo.org/application?number=EP11805824&lng=en&tab=doclist.
Pechenov et al., "Development of an orally delivered GLP-1 receptor agonist through peptide engineering and drug delivery to treat chronic disease," Scientific Reports, Nov. 2021, vol. 11, No. 22521, pp. 1-15.
Wong et al., "Estimation of clinical trial success rates and related parameters," Biostatistics, Jan. 2018, vol. 20, No. 2, pp. 273-286.
Novo Nordisk Reply to Office Action dated Jul. 3, 2008 in EP1863839.
Gomez-Orella, "Strategies to Improve Oral Drug Bioavailability," Expert Opin Drug Deliv, 2005, vol. 2, No. 3: pp. 419-433.
Humphrey, M. J., "The Oral Bioavailability of Peptides and Related Drugs. In Delivery Systems for Peptide Drugs," Davis, S.S., Illum, L., Tomlinson, E., Eds.; Springer Boston, MA, 1986; pp. 139-151.
Novo Nordisk's reply to the examination division dated Nov. 18, 2016 in EP Application 13729743.8, 3 pages.
Novo Nordisk's reply to the opposition grounds of WO2012/080471, corresponding to EP2651398, dated Feb. 15, 2019, 40 pages.
Kwan et al., "Factors Affecting Tablet Disintegration," Journal of the American Pharmaceutical Association, Scientific Edition, Apr. 1957, vol. XLVI, No. 4, pp. 236-239.
Viscasillas i Clerch, "Aportacion al diseno de un nuevo excipiente tipo "coprocessed product" para compresion directa," Universitat de Barcelona, 2008, pp. 159-160.
Pharmaceutical Binders and Their Function in Directly Compressed Tablets, Mechanistic Studies on the Effect of Dry Binders on Mechanical Strength, Pore Structure and Disintegration of Tablets, Dissertation for the Degree of Doctor of Philosophy (Faculty of Pharmacy) in Pharmaceutics presented at Uppsala University in 2000 By Sofia Mattsson, pp. 32-34.
Zhao Na et al., "PYY and obesity (summary)," Sports and Research Education, 2012, vol. 27, No. 3, pp. 102-107.
Huang Lan et al., "Relationship between Peptide Tyrosine-Tyrosine 3-36 and Ingestion Regulation," Hubei Agriculture Sciences, 2009, vol. 48, No. 10, pp. 2591-2594.
Zhao Biqian et al., "Regulation of PYY on Animal Food Intakes," Feed Industry, 2010, vol. 31, No. 18, pp. 51-55.
Beglinger et al. "Pharmacokinetics and pharmacodynamic effects of oral GLP?1 and PYY3?36: a proof?of?concept study in healthy subjects." Clinical Pharmacology & Therapeutics, Oct. 2008, vol. 84, No. 4, pp. 468-474.

(56) References Cited

OTHER PUBLICATIONS

Schmidt et al.,"Effects of PYY3-36 and GLP-1 on energy intake, energy expenditure, and appetite in overweight men." American Journal of Physiology—Endocrinology and Metabolism, Apr. 2014, vol. 306, No. 11, pp. E1248-E1256.

Steinert et al.,"Oral administration of glucagon-like peptide 1 or peptide YY 3-36 affects food intake in healthy male subjects." The American journal of clinical nutrition, Oct. 2010, vol. 92, No. 4, p. 810-817.

Cox Gad, Shayne, "Pharmaceutical Manufacturing Handbook Production and Processes," Hoboken, New Jersey: Wiley-Interscience A John Wiley & Sons, Inc., 2008.

Hancock et al., "The Relative Densities of Pharmaceutical Powders, Blends, Dry Granulations, and Immediate-Release Tablets," Pharmaceutical Technology, Apr. 2003, p. 64-80.

Hoffman et al., "Eligen insulin—a system for the oral delivery of insulin for diabetes," IDrugs, 2008, vol. 11, pp. 433-441.

Lowenthal, Werner, "Disintegration of Tablets" Journal of Pharmaceutical Sciences, Nov. 1972, vol. 61, No. 11, pp. 1695-1711.

Poole, John W., "Effects of Formulation and Dosage Form on Drug Bioavailability" Principles and Perspectives in Drug Bioavailability, Chapter 3, Karger, 1979, pp. 59-89.

Rudnic et al., "Oral Solid Dosage Forms," Chapter 45, Remington—The Science and Practice of Pharmacy, Philadelphia, PA: Lippincott Williams & Wilkins, 2006, Ed. 21st, pp. 889-927.

Tong, W.Q., "Molecular and Physicochemical Properties Impacting Oral Absorption of Drugs" Biopharmaceutics Applications in Drug Development, Chapter 2, Springer, 2008, pp. 26-46.

Study protocol of trial NCT01037582 of Dec. 2009, 7 pages.

Anne Mari Juppo, "Porosity parameters of lactose, glucose and mannitol tablets obtained by mercury porosimetry," International Journal of Pharmaceutics, 1996, vol. 129, pp. 1-12.

Michael E. Aulton., "Aulton's Pharmaceutics. The design and manufacture of medicines" Churchill Livingstone Elsevier, 2007, Ed. 3rd, Chapter 21, pp. 286-303.

Linda Felton, "Remington Essentials of Pharmaceutics," Pharmaceutical Press, 2012, Chapter 6, pp. 63-80 and Chapter 30, pp. 581-610.

Qiu et al., "Developing Solid Oral Dosage Forms" Pharmaceutical Theory and Practice, Academic Press, 2009, 1st Edition, pp. 175-186.

James Swarbrick, "Encyclopedia of Pharmaceutical Technology. vol. 1," Informa Healthcare USA, Inc., 2007, Ed. 3rd, pp. 164-175 and 988-1000.

EP application No. 12160743.6, filed Mar. 22, 2012.

Betts et al., Chapter 14, "Amino Acid Properties and Consequences of Substitutions," Bioinformatics for Geneticists (2003) ed. By Barnes and Gray, John Wiley & Sons, Ltd., pp. 289-316.

Kojima S et al. A role for pancreatic polypeptide in feeding and body weight regulation, "Peptides", Year 2007, vol. 28, No. 2, pp. 459-463.

Lin Shu et al. Critical Role of Arcuate Y4 Receptors and the Melanocortin System in Pancreatic Polypeptide-Induced Reduction in Food Intake in Mice, "PLOS ONE" Year 2009, vol. 4, No. 12, pp. e8488-e8488.

Ito T et al, Effects of peripheral administration of PYY3-36 on feed intake and; plasma acyl-ghrelin levels in pigs, Journal of Endocrinology, Year 2006, vol. 191, pp. 113-119.

Ortiz A. et al, A Novel Long-Acting Selective Neuropeptide Y2 Receptor Polyethylene Glycol-Conjugated Peptide Agonist Reduces Food Intake and Body Weight and Improves Glucose Metabolism in Rodents , The Journal of Pharmacology and Experimental Therapeutics (2007), vol. 323, No. 2, pp. 692-700.

Roger Reidelberger et al., Effects of Glycine-Extended and Serine13-Phosphorylated Forms of Peptide YY on Food Intake in Rats, Peptides, Year 2011; vol. 32, No. 4, pp. 770-775.

Søren L. Pedersen et al., Peptide hormone isoforms: N-terminally branched PYY3-36 isoforms give improved lipid and fat-cell metabolism in diet-induced obese mice, Journal of Peptide Science, Year 2010, vol. 16, Issue 11, pp. 664-673.

Adrian et al., Gut, 1978, vol. 19, No. 10, pp. 907-909.

Heizmann et al., Peptide Research, "Synthesis of an N-3-guanidinopropylglycine (Narg) Derivative as a Versatile Building Block for Solid-Phase Peptide and Peptoid Synthesis", 1994, vol. 7, No. 6, pp. 328-332.

Batterham, R.L. et al., "Gut Hormone PYY3-36 Physiologically Inhibits Food Intake", Nature, 2002, vol. 418, pp. 650-654.

Bowie et al. (Science, 1990, 247:1306-1310).

Burgess et al. (J. Cell Biol. 111:2129-2138, 1990).

Lazar et al. (Mol. Cel. Biol., 8:1247-1252, 1988).

Bork (Genome Research, 2000, 10:398-400).

T.W. Schwartz., "Pancreatic Polypeptide: A Hormone Under Vagal Control", Gastroenterology. 1983, vol. 85, pp. 1411-1425.

Whitcomb. Am. J. Physiol. "Characterization of saturable binding sites for circulating pancreatic polypeptide in rat brain." 1990 vol. 259 G687-G691.

Jorgensen, J. Ch. et al. Euro. J. Pharmacol. "Structure-function studies on neuropeptide Y and pancreatic polypeptide—evidence for two PP-fold receptors in vas deferens" 1990 vol. 186: 105-114.

Cooke, D et al. Nature Reviews. "The obesity pipeline: current strategies in the development of anti-obesity drugs" 2006 vol. 5: 919-930.

Sampson, W.R. J. Pep. Sci. "The Synthesis of 'Difficult' Peptides Using 2-Hydroxy-4-Methoxybenzyl or Pseudoproline Amino Acid Building Blocks: a Comparative Study" 1999 vol. 5: 403.

Knudsen et al. J Med Chem. "Potent Derivatives of Glucagon-Like Peptide-1 with Pharmacokinetic Properties Suitable for Once Daily Administration" 2000. vol. 43(9). p. 1664-1669.

Boggiano, M.M. et al, "PYY3-36 as an anti-obesity drug target", Obesity Reviews. 2005 vol. 6: 307-322.

Dodson, Shontelle et al "Muscle Wasting in Cancer Cachexia: Clinical Implications, Diagnosis, and Emerging Treatment Strategies" Annu. Rev. Med. 2011 vol. 62 pp. 265-279.

Muscaritoli, Maurizio et al "Prevention and Treatment of Cancer Cachexia: New Insights into an Old Problem." European Journal of Cancer, 2006 vol. 42 pp. 31-41.

Soeren L. Pedersen et al., Peptide hormone isoforms: N-terminally branched PYY3-36 isoforms give improved lipid and fat-cell metabolism in diet-induced obese mice, Journal of Peptide Science, Year 2010, vol. 16, Issue 11, pp. 664-673.

Van den Hoek A. et al., Chronic PYY3-36 treatment promotes fat oxidation and ameliorates insulin resistance in C57BL6 mice, American Journal of Physiology—Endocrinology and Metabolism, Year 2007, vol. 292, No. 1 pp. E238-E245.

Kouki Kitagawa et al: Solution synthesis of human peptide YY(hPYY),Chemical & Pharmaceutical Bulletin,Year Jun. 1, 1990 vol. 38, No. 6, pp. 1731-1734.

Ortiz A. et a lA Novel Long-Acting Selective Neuropeptide Y2 Receptor Polyethylene Glycol-Conjugated Peptide Agonist Reduces Food Intake and Body Weight and Improves Glucose Metabolism in Rodents, The Journal of Pharmacology and Experimental Therapeutics Year 2007, vol. 323 No. 2, pp. 692-700.

Roger Reidelberger et al: "Effects of glycine-extended and serine-phosphorylated forms of peptide YY on food intake in rats", Peptides,Peptides Year 2011,vol. 32, No. 4, pp. 770-775.

Van den Hoek A. et al Chronic PYY3-36 treatment promotes fat oxidation and ameliorates insulin resistance in C57BL6 mice American Journal of Physiological Endocrinology and Metabolism Year 2006,vol. 292, No. 1 pp. E238-E245.

Balasubramaniam et al., "Structure-Activity Studies Including a psi(CH2—NH) Scan of Peptide YY (PYY) Active Site, PYY(22-36), for Interaction with Rat Intestinal PYY Receptors: Development of Analogues with Potent in Vivo Activity in the Intestine," J. Med. Chem., 2000, vol. 43, pp. 3420-3427.

Atherosclerosis, from http://www.merckmanuals.com/professional/cardiovascular-disorders/arteriosclerosis/atherosclerosis, pp. 1-14, accessed Dec. 29, 2015.

Diabetes, from http://www.merckmanuals.com/professional/endocrine-and-metabolic-disorders/ . . . , pp. 1-34, accessed Sep. 2, 2016.

Dyslipidemia, from http://www.merckmanuals.com/professional/endocrine-and-metabolic-disorders/lipid-dis . . . , pp. 1-11, accessed Dec. 29, 2015.

(56) References Cited

OTHER PUBLICATIONS

Fatty Liver Disease, from http://www.webmd.com/hepatitis/fatty-liver-disease?page=2&print=true, pp. 1-4, accessed Dec. 29, 2015.
Nabel, "Cardiovascular Disease," New Engl. J. Med., 2003, vol. 349, pp. 60-72.
Neary et al., "Peptide YY: Food for thought," Physiology & Behavior 97: 616-619 (2009).
Nonatheromatous Arteriosclerosis, from http://www.merckmanuals.com/professional/cardiovascular-disorders/arteriosclerosis/non . . . , pp. 1-2, accessed Dec. 29, 2015.
Sam et al., "Selective Ablation of Peptide YY Cells in Adult Mice Reveals Their Role in Beta Cell Survival," Gastroenterology, 143:459-468 (2012).
Vincent et al., "The satiety hormone peptide YY as a regulator of appetite," J Clin Pathol 61 :548-552 (2008).
Extract of the opposed patent EP2863895 reterieved on Jan. 13, 2022, 2 pages, full prosecution file can be found In European Patent register https://register.epo.org/application?number=EP13729743&Ing=en&tab=doclist.
Kamiji, M.M et al., "NPY Y2 and Y4 receptors selective ligands: promising anti-obesity drugs?", Current Topics in Medical Chemistry, 2007, vol. 7, pp. 1734-1742.
Sainsbury, A. et al., "Synergistic Effects of Y2 and Y4 Receptors on Adiposity and Bone Mass Revealed in Double Knockout Mice", Mol Nad Cell Biol, Aug. 2003, vol. 23, pp. 5225-5233.
Tokuriki et al., "Stability effects of mutations and protein evolvability", Current Opinion in Structural Biology, Oct. 2009, vol. 19, No. 5, pp. 596-604.
Nauck et al., "The once-weekly human GLP-1 analogue semaglutide provides significant reductions in HbA1c and body weight in patients with type 2 diabetes," Abstract 2, Diabetologia, 2012, vol. 55, Suppl. 1, page S7.
Kapitza et al., "Oral Insulin: A Comparison with Subcutaneous Regular Human Insulin in Patients with Type 2 Diabetes", Diabetes Care, Jun. 2010, vol. 33, No. 6, pp. 1288-1290.
Mousa et al., "Pharmacokinetics and Pharmacodynamics of Oral Heparin Solid Dosage Form in Healthy Human Subjects," J. Clinical Pharmacology, Dec. 2007, vol. 47, No. 12, pp. 1508-1520.
Goodman & Gilman's the Pharmacological Basis of Therapeutics, 1996, 9th Edition. Table of Contents Only.
Hamdy et al., "Oral Calcitonin", Int'l J. Women's Health, 2012, pp. 471-479.
Knudsen et al., "GLP-1 Derivatives as Novel Compounds for the Treatment of Type 2 Diabetes: Selection of NN2211 for Clinical Development", Drugs Future, 2001, vol. 26, No. 7, pp. 677-685.
Manandhar et al., "Glucagon-like Peptide-I (GLP-1) Analogs: Recent Advances, New Possibilities, and Therapeutic Implications", J. of Med. Chem., Oct. 2014, vol. 58, pp. 1020-1037.

\* cited by examiner

ORAL DOSING OF GLP-1 COMPOUNDS

CROSS-REFERENCE TO RELATED APPLICATIONS

This application is a Continuation of U.S. application Ser. No. 15/651,043, filed Jul. 17, 2017, which is a Continuation of U.S. application Ser. No. 14/785,493, filed Oct. 19, 2015, which is a 35 U.S.C. § 371 National Stage application of International Application PCT/EP2014/058974, filed May 2, 2014, which claims priority to European Patent Application 13166205.8, filed May 2, 2013; all of which are hereby incorporated by reference.

TECHNICAL FIELD

The present invention relates to improved uses of GLP-1 peptides in oral therapy.

BACKGROUND

The oral route is by far the most widely used route for drug administration. Administration of peptides and proteins, such as GLP-1 peptides, is however often limited to parenteral routes rather than the preferred oral administration due to several barriers, such as enzymatic degradation in the gastrointestinal tract and intestinal mucosa, insufficient absorption from the intestinal mucosa, as well as first pass metabolism in the liver.

WO2007/024700 relates to methods for reducing body weight and treating diabetes by the use of exendin peptides.

There is thus a need for an improved method for administering or use of GLP-1 peptides by the oral route where variability in plasma concentration is acceptable.

SUMMARY

In some embodiments the present invention relates to a solid composition comprising a GLP-1 peptide and an enhancer for use as a medicament by oral administration, wherein said peptide has plasma half-life in humans of at least 60 hours, wherein said composition is administered at least 3 times, and wherein a) said composition is administered every second day or more often; or b) said composition is administered such that the ratio between the plasma half-life in days in humans of said peptide and the dosing interval in days of said composition is more than 2:1.

In some embodiments the present invention relates to a method of medical treatment comprising orally administering to a patient in need thereof a solid composition comprising a GLP-1 peptide and an enhancer, wherein said peptide has plasma half-life in humans of at least 60 hours, wherein said composition is administered at least 3 times, and wherein a) said composition is administered every second day or more often; or b) said composition is administered such that the ratio between the plasma half-life in days in humans of said peptide and the dosing interval in days of said composition is more than 2:1.

The invention may also solve further problems that will be apparent from the disclosure of the exemplary embodiments.

The method or use of the invention comprises administration of a GLP-1 peptide, e.g. to a subject in need thereof. In some embodiments the GLP-1 peptide is administered in an amount in the range of 0.5-100 mg, such as in the range of 0.5-50 mg or 0.5-25 mg. In some embodiments the GLP-1 peptide is administered in an amount in the range of 1-25 mg or 5-50 mg. In some embodiments the GLP-1 peptide is administered in an amount in the range of 0.5-10 mg or 0.5-5 mg. In some embodiments the GLP-1 peptide is administered in a dosage which provides a steady state average plasma concentration of said peptide of 1-1000 nM, such as 1-300 nM or 10-100 nM.

DESCRIPTION

The present invention relates to methods (such as dosing regimens) of orally administering a GLP-1 peptide having a plasma half-life in humans of at least 60 hours or, in other words, to an improved use of said GLP-1 peptide in therapy for treatment of e.g. type 2 diabetes. The GLP-1 peptide may be administered in a solid dosage form, such as a tablet.

GLP-1 peptides with a plasma half-life in humans of at least 60 hours would have been expected to be preferred included in an oral dosing regimen with a low frequency of administration, e.g. once weekly administration; such dosing regimens are for example used for once weekly s.c. administration of the GLP-1 peptide semaglutide. For example, semaglutide can be administered by injection, such as s.c. injection, in the form of an aqueous composition comprising 1.34 mg/ml semaglutide, 1.42 mg/ml disodium hydrogen phosphate dihydrate, 14.0 mg/ml propylene glycol, 5.50 mg/ml phenol, pH 7.4; where pH is adjusted using hydrochloric acid and/or sodium hydroxide. Alternatively, semaglutide can be administered by injection, such as s.c. injection, in the form of an aqueous composition comprising 4.1 mg/ml semaglutide, 1.42 mg/ml disodium hydrogen phosphate dihydrate, 14.0 mg/ml propylene glycol, 5.50 mg/ml phenol, pH 7.4; where pH is adjusted using hydrochloric acid and/or sodium hydroxide.

However, it has by the inventors surprisingly been found that the variability in plasma concentration of a GLP-1 peptide is lower when dosing GLP-1 peptide according to methods or uses of the invention. The present invention may be seen as dosing regimens for oral administration of a GLP-1 peptide having a plasma half-life in humans of at least 60 hours comprising oral administration of said GLP-1 peptide more often than the half-life of said GLP-1 peptide would suggest, wherein said GLP-1 peptide may be administered in a solid dosage form, such as a tablet.

The following non-limiting example further illustrates one aspect of the invention: Once daily oral administration of a tablet comprising the GLP-1 peptide semaglutide provides surprisingly lower variability in the plasma concentration of said peptide when administered for a period of time (e.g. for a month) as compared to oral administration of said peptide using an alternative dosing regimen for the same period of time (e.g. a dosing regimen using once weekly administration). Examples 1-3 herein show that, surprisingly, daily oral administration of a tablet comprising a GLP-1 peptide provides reduced variability in plasma concentration. It is expected that a dosing regimen using once weekly administration of a GLP-1 peptide would result in variability in plasma concentration of the GLP-1 peptide in a similar range to that of a single dose administration.

When using a GLP-1 peptide according to a method or use of the invention, the variability in plasma concentration of the GLP-1 peptide is thus surprisingly lower when measuring the plasma concentration of the GLP-1 peptide after each dose to a population and comparing the measurements than when making similar measurements after an alternative dosing regimen.

In some embodiments the invention relates to certain oral dosing regimens of GLP-1 peptides which provide improvement in variability in plasma concentration of said GLP-1 peptide. In some embodiments the GLP-1 peptide is administered by a dosing regimen which provides an improved variability compared to administration following an alternative dosing regimen.

Reduction in the variability in plasma concentration and hence lower difference between minimum and maximum plasma concentrations in a population and/or in a patient would lead to less GLP-1 related side effects (such as nausea and vomiting) and better effect of the medical treatment (such as reduction in blood glucose and body weight).

In some embodiments the invention relates to a solid composition comprising a GLP-1 peptide and an enhancer for use as a medicament by oral administration, wherein said peptide has plasma half-life in humans of at least 60 hours, wherein said composition is administered at least 3 times, and wherein said composition is administered every second day or more often. In some embodiments the present invention relates to a method of medical treatment comprising orally administering to a patient in need thereof a solid composition comprising a GLP-1 peptide and an enhancer, wherein said peptide has plasma half-life in humans of at least 60 hours, wherein said composition is administered at least 3 times, and wherein said composition is administered every second day or more often.

In some embodiments the method or use of the invention comprises administration twice daily, once daily, or every second day. In some embodiments the method or use of the invention comprises administration at least every second day (i.e. administration every second day or more often), at least once daily, or at least twice daily.

The reduction in variation is not expected to occur until after a few administrations using the dosing regimen of the invention. Accordingly, in some embodiments the method or use of the invention is carried out for a period of time, such as administration at least 3 times. In some embodiments the method or use comprises administration at least 5 times or at least 7 times. In some embodiments the method or use comprises administration at least 10 times, at least 14 times or at least 21 times. In some embodiments the method or use is carried for a period of at least 2 weeks, at least 3 weeks, or at least 4 weeks.

The variability is evaluated by comparing the plasma concentration level (i.e. $C_{max}$, AUC or $C_{average}$) in a dosing interval (i.e. from one oral dosing to the next oral dosing). In some embodiments the term "variability" is herein, when used in connection with plasma concentration of a GLP-1 peptide, meant to mean the % CV in GLP-1 peptide plasma concentration level (i.e. $C_{max}$, AUC or $C_{average}$) in a dosing interval. In some embodiments the term "variability" is herein, when used in connection with plasma concentration of a GLP-1 peptide, meant to mean the % CV or % RSD in GLP-1 peptide plasma concentration level (i.e. $C_{max}$, AUC or $C_{average}$) after each dosing to a population.

In some embodiments the methods or uses of the invention are particularly suitable for orally administering a GLP-1 peptide for which the bioavailability is low. A low bioavailability may be a bioavailability of less than 10%. As used herein, the term "bioavailability" of a compound refers to the plasma concentration of said compound administered orally relative to the plasma concentration of the same amount of said compound administered intravenously.

In some embodiments the invention relates to a method or use of oral administration of a pharmaceutically active GLP-1 peptide to a subject, wherein said peptide has plasma half-life in humans of at least 60 hours, and wherein said method comprises the step of administering said peptide every second day or more often in a therapeutically effective amount. In some embodiments of the invention, the plasma half-life of the GLP-1 peptide in humans is about 70 hours, and said method comprises the step of administering said peptide every second day or more often in a therapeutically effective amount. In some embodiments the plasma half-life the GLP-1 peptide in humans is at least 100 hours, and said method comprises the step of administering said peptide every second day or more often in a therapeutically effective amount. In some embodiments the plasma half-life the GLP-1 peptide in humans is at least 120 hours, and said method comprises the step of administering said peptide every second day or more often in a therapeutically effective amount. In some embodiments the plasma half-life the GLP-1 peptide in humans is at least 160 hours, and said method comprises the step of administering said peptide every second day or more often in a therapeutically effective amount.

In some embodiments the invention relates to a GLP-1 peptide for use as an oral pharmaceutical every second day or more often in the treatment of diabetes, wherein said peptide has plasma half-life in humans of at least 60 hours. In some embodiments the invention relates to a GLP-1 peptide for use as an oral pharmaceutical every second day or more often in the treatment of diabetes, wherein said peptide has plasma half-life in humans of at least 70 hours. In some embodiments the invention relates to a GLP-1 peptide for use as an oral pharmaceutical every second day or more often in the treatment of diabetes, wherein said peptide has plasma half-life in humans of at least 100 hours. In some embodiments the invention relates to a GLP-1 peptide for use as an oral pharmaceutical every second day or more often in the treatment of diabetes, wherein said peptide has plasma half-life in humans of at least 120 hours. In some embodiments the invention relates to a GLP-1 peptide for use as an oral pharmaceutical every second day or more often in the treatment of diabetes, wherein said peptide has plasma half-life in humans of at least 160 hours.

By "plasma half-life" is herein meant the period of time it takes after administration (i.v. (intra venously) or p.o. (per os)) to halve the plasma concentration, measured after the initial distribution phase.

In some embodiments an "effective amount" of a GLP-1 peptide as used herein means an amount sufficient to cure, alleviate, or partially arrest the clinical manifestations of a given disease or state and its complications. An amount adequate to accomplish this is defined as "effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician or veterinary.

In some embodiments the term "treatment" or "treating" as used herein means the management and care of a patient for the purpose of combating a condition, such as a disease or a disorder. In some embodiments the term "treatment" or "treating" is intended to include the full spectrum of treatments for a given condition from which the patient is suffering, such as administration of the active GLP-1 peptide to alleviate the symptoms or complications; to delay the progression of the disease, disorder, or condition; to alleviate or relieve the symptoms and complications; and/or, to cure or eliminate the disease, disorder, or condition as well as to prevent the condition. In some embodiments prevention is to be understood as the management and care of a patient for the purpose of combating the disease, condition, or disorder and includes the administration of the active GLP-1 peptide to prevent the onset of the symptoms or complications.

In some embodiments the variability is less than 100%, i.e. the plasma concentration varies from one dosing to the next dosing by less than 100%. In some embodiments the variability in plasma concentration is 90% or less, alternatively 80% or less, alternatively 70% or less when comparing plasma concentration of GLP-1 from one dosing to the next dosing. In some embodiments the variability in plasma concentration is 60% or less, alternatively 50% or less, alternatively 40% or less when comparing plasma concentration of GLP-1 from one dosing to the next dosing. In some embodiments the variability is determined based on a population of at least 5 subjects, such as at least 10 subjects.

With the term "alternative dosing regimen" is herein meant a dosing regimen falling outside the claimed method. In some embodiments the term "alternative dosing regimen" as used herein is a dosing regimen (i.e. a method or use) comprising a dosing interval selected from the group consisting of a single administration, administration once weekly or less frequently, or administration every second week or less frequently.

In some embodiments the invention relates to a solid composition comprising a GLP-1 peptide and an enhancer for use as a medicament by oral administration, wherein said peptide has plasma half-life in humans of at least 60 hours, wherein said composition is administered at least 3 times, and wherein said composition is administered such that the ratio between the plasma half-life in days in humans of said peptide and the dosing interval in days of said composition is more than 2:1. In some embodiments the present invention relates to a method of medical treatment comprising orally administering to a patient in need thereof a solid composition comprising a GLP-1 peptide and an enhancer, wherein said peptide has plasma half-life in humans of at least 60 hours, wherein said composition is administered at least 3 times, and wherein said composition is administered such that the ratio between the plasma half-life in days in humans of said peptide and the dosing interval in days of said composition is more than 2:1.

In some embodiments the invention relates to a method or use of oral administration of a low clearance GLP-1 peptide is administered to a subject, wherein the ratio between the plasma half-life in days in humans of said peptide and the dosing interval in days of said peptide is 2:1 or more, such as 3:1 or more or 4:1 or more. 74. In some embodiments the ratio between the plasma half-life in days in humans of the GLP-1 peptide and the dosing interval in days of said peptide is more than 5:1 or more than 6:1. In some embodiments the ratio between the plasma half-life in days in humans of the GLP-1 peptide and the dosing interval in days of said peptide is more than 7:1 or more than 14:1. In some embodiments of the invention, a method or use of oral administration is described wherein a low clearance GLP-1 peptide in a therapeutically effective dosage is administered to a subject, wherein the ratio between the plasma half-life in days in humans of said peptide and the dosing interval in days of said peptide is 2:1 or more. Thus, when the plasma half-life of said GLP-1 peptide is e.g. 2 days in humans the dosing interval in days of said peptide is 1 or less, i.e. the peptide is dosed at least once per day; when the plasma half-life of said GLP-1 peptide is e.g. 4 days in humans the dosing interval in days of said peptide is 2 or less, i.e. the peptide is dosed at least once per 2 days; etc. In some embodiments the invention relates to a method or use of oral administration is described wherein a low clearance GLP-1 peptide in a therapeutically effective dosage is administered to a subject, wherein the ratio between the plasma half-life in days in humans of said peptide and the dosing interval in days of said peptide is 2:1 or more. In some embodiments the term "therapeutically effective dosage" refers to an administration comprising a therapeutically effective amount of GLP-1 peptide.

When used herein the term "low clearance GLP-1 peptide" or "low clearance GLP-1" shall mean a GLP-1 peptide which has a long plasma half-life in standard models of pharmacokinetics (e.g. pharmacokinetics in Beagle dogs, in pigs or in humans) compared to the GLP-1 peptide "liraglutide". In some embodiments the term "long plasma half-life" refers to a half-life which is longer than the half-life of liraglutide, wherein the half-life may be determined as described in the section herein with the title "Method for Determining Plasma Half-Life". In some embodiments the term "long plasma half-life" refers to a half-life in humans which is at least 60 hours, at least 70 hours, or at least 80 hours.

In some embodiments the method or use of oral administration of the invention results in reduced side effects relative to when using an alternative dosing regimen. In some embodiments the method of oral administration of the invention results in reduction in nausea and/or vomiting relative to when using an alternative dosing regimen. In some embodiments the method of oral administration of the invention results in reduction in nausea relative to when using an alternative dosing regimen. In some embodiments the method of oral administration of the invention results in reduction in vomiting relative to when using an alternative dosing regimen.

Method for Determining Plasma Half-Life

A pharmacokinetic study may be carried out to determine plasma half-life of the GLP-1 peptides after i.v. and/or p.o. administration to humans or animals (such as e.g. Beagle dogs). In some embodiments the plasma half-life of the GLP-1 peptide is determined in humans after i.v. administration. In some embodiments the plasma half-life of the GLP-1 peptide is determined in humans after p.o. administration.

In such study, subjects are typically administered a single dose i.v. or p.o. of the GLP-1 peptide in a relevant formulation. Blood samples are drawn at predefined time points after dosing, and samples are analysed for concentration of GLP-1 peptide with a relevant quantitative assay. Based on these measurements plasma concentration versus time profile are plotted and a so-called non-compartmental pharmacokinetic analysis of the data is performed.

For most active ingredients, the terminal part of the plasma-concentration profiles will be linear when drawn in a semi-logarithmic plot, reflecting that after the initial absorption and distribution, drug is removed from the body at a constant fractional rate. The rate (lambda Z or $\lambda_z$) is equal to minus the slope of the terminal part of the plot. From this rate, also a plasma half-life may be calculated, as $t\frac{1}{2}=\ln(2)/\lambda_z$ (see, e.g., Johan Gabrielsson and Daniel Weiner: Pharmacokinetics and Pharmacodynamic Data Analysis. Concepts & Applications, 3rd Ed., Swedish Pharmaceutical Press, Stockholm (2000)).

The plasma concentration of GLP-1 peptides may be determined using any suitable method. The concentration in plasma of the GLP-1 peptides for the method or use of the invention may be determined using any suitable method. For example, LC-MS (Liquid Chromatography Mass Spectroscopy) may be used, or immunoassays such as RIA (Radio Immuno Assay), ELISA (Enzyme-Linked Immuno Sorbent Assay), and LOCI (Luminescence Oxygen Channeling Immunoassay). General protocols for suitable RIA and ELISA assays are found in, e.g., WO2009/030738 on p. 116-118. The plasma concentration of GLP-1 peptides may be determined using the LOCI method described herein in the experimental section titled "Analysis of Plasma Samples using LOCI". The plasma concentration of GLP-1 peptides may be determined using the LC-MS method described herein in the experimental section titled "Alternative Analysis of Plasma Samples using LC-MS".

Method for Determining Variability in Plasma Concentration

A pharmacokinetic study may be carried out to determine plasma half-life of the GLP-1 peptide after i.v. and/or p.o. administration to humans or animals (such as e.g. Beagle dogs). In such study, subjects are typically administered one or multiple doses p.o. of the GLP-1 peptide in a relevant formulation. Blood samples are drawn at predefined time points after dosing, and samples are analysed for concentration of active ingredient with a relevant quantitative assay. Based on these measurements plasma concentration versus time profile are plotted and a so-called non-compartmental pharmacokinetic analysis of the data is performed. The variability in plasma concentration can be determined as the % CV or % RSD for either $C_{max}$ or $C_{average}$ or AUC. For example, the variability in plasma concentration can be determined as the % CV for either $C_{max}$ or $C_{average}$ or AUC.

GLP-1 Peptide

The method or use of the present invention comprises a GLP-1 peptide with a plasma half-life in humans of at least 60 hours. The terms "GLP-1 peptide" and "active GLP-1 peptide" as used herein mean a peptide which is either human GLP-1 or an analogue or a derivative thereof with GLP-1 activity.

The term "human GLP-1" or "native GLP-1" as used herein means the human GLP-1 hormone whose structure and properties are well-known. Human GLP-1 is also denoted GLP-1(7-37), it has 31 amino acids and is the result from selective cleavage of the proglucagon molecule.

The GLP-1 peptides of the invention have GLP-1 activity. This term refers to the ability to bind to the GLP-1 receptor and initiate a signal transduction pathway resulting in insulinotropic action or other physiological effects as is known in the art. For example, the analogues and derivatives of the invention can be tested for GLP-1 activity using a standard GLP-1 activity assay.

The term "GLP-1 analogue" as used herein means a modified human GLP-1 wherein one or more amino acid residues of human GLP-1 have been substituted by other amino acid residues and/or wherein one or more amino acid residues have been deleted from human GLP-1 and/or wherein one or more amino acid residues have been added and/or inserted to human GLP-1.

In some embodiments the GLP-1 peptide has plasma half-life in humans of at least 60 hours, such as at least about 70 hours, at least 90 hours, at least 100 hours, or such as at least 120 hours, at least 140 hours or at least 160 hours. In some embodiments the GLP-1 peptide has plasma half-life in humans of at least 60 hours, at least 70 hours or at least 90 hours. In some embodiments the GLP-1 peptide has plasma half-life in humans of at least 100 hours, or such as at least 120 hours, at least 140 hours or at least 160 hours. In some embodiments the GLP-1 peptide has plasma half-life in humans of at least 1 day, at least 36 hours or at least 2 days.

In some embodiments a GLP-1 analogue comprises 10 amino acid modifications (substitutions, deletions, additions (including insertions) and any combination thereof) or less relative to human GLP-1, alternatively 9, 8, 7, 6, 5, 4, 3 or 2 modifications or less, yet alternatively 1 modification relative to human GLP-1. In some embodiments a GLP-1 analogue comprises 5 amino acid modifications (substitutions, deletions, additions (including insertions) and any combination thereof) or less relative to human GLP-1.

Modifications in the GLP-1 molecule are denoted stating the position, and the one or three letter code for the amino acid residue substituting the native amino acid residue.

When using sequence listing, the first amino acid residue of a sequence is assigned no. 1. However, in what follows—according to established practice in the art for GLP-1 peptides—this first residue is referred to as no. 7, and subsequent amino acid residues are numbered accordingly, ending with no. 37. Therefore, generally, any reference herein to an amino acid residue number or a position number of the GLP-1(7-37) sequence is to the sequence starting with His at position 7 and ending with Gly at position 37. Using the one letter codes for amino acids, terms like 34E, 34Q, or 34R designates that the amino acid in the position 34 is E, Q and R, respectively. Using the three letter codes for amino acids, the corresponding expressions are 34Glu, 34Gln and 34Arg, respectively.

By "des7" or "(or Des$^7$)" is meant a native GLP-1 lacking the N-terminal amino acid, histidine. Thus, e.g., des7GLP-1(7-37) is an analogue of human GLP-1 where the amino acid in position 7 is deleted. This analogue may also be designated GLP-1(8-37). Similarly, (des7+des8); (des7, des8); (des7-8); or (Des$^7$, Des$^8$) in relation to an analogue of GLP-1(7-37), where the reference to GLP-1(7-37) may be implied, refers to an analogue in which the amino acids corresponding to the two N-terminal amino acids of native GLP-1, histidine and alanine, have been deleted. This analogue may also be designated GLP-1(9-37).

A non-limiting example of an analogue of the invention is [Aib$^8$,Arg$^{34}$]GLP-1(7-37), which designates a GLP-1(7-37) analogue, in which the alanine at position 8 has been substituted with α-aminoisobutyric acid (Aib) and the lysine at position 34 has been substituted with arginine. This analogue may also be designated (8Aib, R34) GLP-1(7-37).

The term "GLP-1 derivative" as used herein means a chemically modified parent GLP-1(7-37) or an analogue thereof, wherein the modification(s) are in the form of attachment of amides, carbohydrates, alkyl groups, acyl groups, esters, PEGylations, combinations thereof, and the like.

In some embodiments of the invention the modification(s) include attachment of a side chain to GLP-1(7-37) or an analogue thereof. In a particular aspect, the side chain is capable of forming non-covalent aggregates with albumin, thereby promoting the circulation of the derivative with the blood stream, and also having the effect of protracting the time of action of the derivative, due to the fact that the aggregate of the GLP-1-derivative and albumin is only slowly disintegrated to release the active peptide ingredient. Thus, the substituent, or side chain, as a whole is preferably referred to as an albumin binding moiety. In particular aspects, the side chain has at least 10 carbon atoms, or at least 12, 14, 16, 18, 20, 22, or at least 24 carbon atoms. In further particular aspects, the side chain may further include at least 5 hetero atoms, in particular O and N, for example at least 7, 9, 10, 12, 15, 17, or at least 20 hetero atoms, such as at least 1, 2, or 3 N-atoms, and/or at least 3, 6, 9, 12, or 15 O-atoms. In some embodiments the GLP-1 peptide is an acylated GLP-1 peptide.

In some embodiments the albumin binding moiety comprises a portion which is particularly relevant for the albumin binding and thereby the protraction, which portion may accordingly be referred to as a "protracting moiety". The protracting moiety may be at, or near, the opposite end of the albumin binding moiety, relative to its point of attachment to the peptide.

In some embodiments the albumin binding moiety comprises a portion in between the protracting moiety and the point of attachment to the peptide, which portion may be referred to as a "linker", "linker moiety", "spacer", or the like. The linker may be optional, and hence in that case the albumin binding moiety may be identical to the protracting moiety.

In some embodiments the albumin binding moiety and/or the protracting moiety is lipophilic, and/or negatively charged at physiological pH (7.4).

The albumin binding moiety, the protracting moiety, or the linker may e.g. be covalently attached to a lysine residue of the GLP-1 peptide by acylation. In a preferred aspect, an active ester of the albumin binding moiety, preferably comprising a protracting moiety and a linker, is covalently linked to an amino group of a lysine residue, preferably the epsilon amino group thereof, under formation of an amide bond (this process being referred to as acylation).

Unless otherwise stated, when reference is made to an acylation of a lysine residue, it is understood to be to the epsilon-amino group thereof.

For the present purposes, the terms "albumin binding moiety", "protracting moiety", and "linker" may include the unreacted as well as the reacted forms of these molecules. Whether or not one or the other form is meant is clear from the context in which the term is used.

For the attachment to the GLP-1 peptide, the acid group of the fatty acid, or one of the acid groups of the fatty diacid, forms an amide bond with the epsilon amino group of a lysine residue in the GLP-1 peptide, preferably via a linker.

The term "fatty diacid" refers to fatty acids as defined above but with an additional carboxylic acid group in the omega position. Thus, fatty diacids are dicarboxylic acids.

Each of the two linkers of the derivative of the invention may comprise the following first linker element:

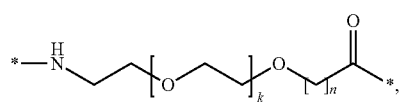

Chem I wherein k is an integer in the range of 1-5, and n is an integer in the range of 1-5.

In a particular aspect, when k=1 and n=1, this linker element may be designated OEG, or a di-radical of 8-amino-3,6-dioxaoctanic acid, and/or it may be represented by the following formula:

NH—(CH₂)₂—O—(CH₂)₂—O—CH₂—CO—*    Chem II:

In another particular aspect, each linker of the derivative of the invention may further comprise, independently, a second linker element, preferably a Glu di-radical, such as Chem III and/or Chem IV:

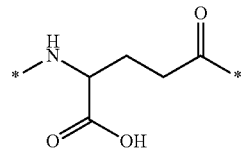

Chem III

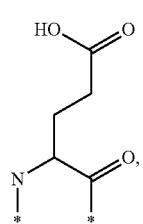

Chem IV wherein the Glu di-radical may be included p times, where p is an integer in the range of 1-3.

Chem III may also be referred to as gamma-Glu, or briefly γGlu, due to the fact that it is the gamma carboxy group of the amino acid glutamic acid which is here used for connection to another linker element, or to the epsilon-amino group of lysine. As explained above, the other linker element may, for example, be another Glu residue, or an OEG molecule. The amino group of Glu in turn forms an amide bond with the carboxy group of the protracting moiety, or with the carboxy group of, e.g., an OEG molecule, if present, or with the gamma-carboxy group of, e.g., another Glu, if present.

Chem IV may also be referred to as alpha-Glu, or briefly aGlu, or simply Glu, due to the fact that it is the alpha carboxy group of the amino acid glutamic acid which is here used for connection to another linker element, or to the epsilon-amino group of lysine.

The above structures of Chem. III and Chem. IV cover the L-form, as well as the D-form of Glu. In particular aspects, Chem. III and/or Chem. IV is/are, independently, a) in the L-form, or b) in the D-form.

In still further particular aspects the linker has a) from 5 to 41 C-atoms; and/or b) from 4 to 28 hetero atoms.

The concentration in plasma of the GLP-1 derivatives of the invention may be determined using any suitable method. For example, LC-MS (Liquid Chromatography Mass Spectroscopy) may be used, or immunoassays such as RIA (Radio Immuno Assay), ELISA (Enzyme-Linked Immuno Sorbent Assay), and LOCI (Luminescence Oxygen Channeling Immunoassay). General protocols for suitable RIA and ELISA assays are found in, e.g., WO09/030738 on p. 116-118.

The conjugation of the GLP-1 analogue and the activated side chain is conducted by use of any conventional method, e.g. as described in the following references (which also describe suitable methods for activation of polymer molecules): R. F. Taylor, (1991), "Protein immobilisation. Fundamental and applications", Marcel Dekker, N.Y.; S. S. Wong, (1992), "Chemistry of Protein Conjugation and Crosslinking", CRC Press, Boca Raton; G. T. Hermanson et al., (1993), "Immobilized Affinity Ligand Techniques", Academic Press, N.Y.). The skilled person will be aware that the activation method and/or conjugation chemistry to be used depends on the attachment group(s) of the polypeptide (examples of which are given further above), as well as the functional groups of the polymer (e.g. being amine, hydroxyl, carboxyl, aldehyde, sulfydryl, succinimidyl, maleimide, vinysulfone or haloacetate).

In some embodiments of the invention, the GLP-1 peptide is N-epsilon26-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl][Aib8,Arg34]GLP-1-(7-37) (alternatively named N$^{6,26}$-{18-[N-(17-carboxyheptadecanoyl)-L-γ-glutamyl]-10-oxo-3,6,12,15-tetraoxa-9,18-diazaoctadecanoyl}-[8-(2-amino-2-propanoic acid),34-L-arginine] human glucagon-like peptide 1(7-37)) or N$^{\varepsilon 26}${2-[2-(2-{2-[2-(2-{(S)-4-Carboxy-4-[10-(4-carboxyphenoxy)decanoylamino]butyrylamino}ethoxy)ethoxy]-acetylamino}ethoxy)ethoxy]acetyl}, N$^{\varepsilon 37}$-{2-[2-(2-{2-[2-(2-{(S)-4-carboxy-4-[10-(4-carboxy-phenoxy)decanoylamino]butyrylamino}ethoxy)ethoxy]acetylamino}ethoxy)ethoxy]acetyl}-[Aib$^8$,Arg$^{34}$, Lys$^{37}$] GLP-1 (7-37)-OH.

In some embodiments of the invention, the GLP-1 peptide is N-epsilon26-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl][Aib8,Arg34]GLP-1-(7-37).

In some embodiments of the invention, the GLP-1 peptide is N$^{\varepsilon 26}${2-[2-(2-{2-[2-(2-{(S)-4-Carboxy-4-[10-(4-carboxyphenoxy)decanoylamino]butyrylamino}ethoxy)ethoxy]acetylamino}-ethoxy)ethoxy]acetyl}, N$^{\varepsilon 37}$-{2-[2-(2-{2-[2-(2-{(S)-4-carboxy-4-[10-(4-carboxyphenoxy)decanoylamino]butyrylamino}ethoxy)ethoxy]acetylamino}ethoxy)ethoxy]acetyl}-[Aib$^8$,Arg$^{34}$,Lys$^{37}$] GLP-1(7-37)-OH.

Enhancer

The method or use of the present invention may comprise an enhancer. In some embodiments the enhancer is water soluble. In some embodiments the term "enhancer" refers to a compound which increases the bioavailability of the GLP-1 peptide of the composition following oral administration. Accordingly, in some embodiments the enhancer is a bioavailability enhancer. In some embodiments the weight percentage of the enhancer is at least 60% (w/w), such as at least 70% (w/w) or at least 75% (w/w), of the total weight of the composition.

The enhancer may be a medium chain fatty acid or a salt thereof and has a carbon chain length of from about 4 to about 20 carbon atoms. In some embodiments the enhancer is a salt of capric acid, such as sodium caprate. In some embodiments the weight percentage of said medium chain fatty acid, such as a salt of capric acid (e.g. sodium caprate), is at least 60% (w/w), such as at least 70% (w/w) or at least 75% (w/w), of the total weight of the composition. In some embodiments the amount of said medium chain fatty acid, such as a salt of capric acid (e.g. sodium caprate), in the composition is at least 2.0 mmol, such as at least 2.5 mmol or at least 3.5 mmol, in one dosage unit. In some embodiments the amount of a salt of capric acid, such as sodium caprate, in the composition is at least 300 mg, at least 400 mg, or at least 500 mg.

In some embodiments the enhancer is a salt of N-(8-(2-hydroxybenzoyl)amino)caprylic acid. In some embodiments the enhancer is an absorption enhancer. The structural formula of N-(8-(2-hydroxybenzoyl)amino)caprylate is shown in formula (I).

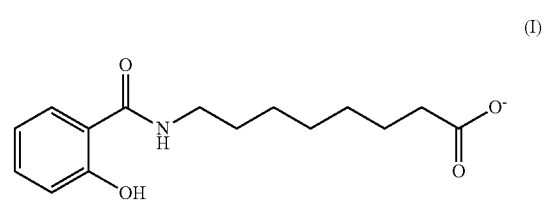 [SMILES: O=C([O-])CCCCCCCNC(=O)c1ccccc1O]

(I)

In some embodiments the salt of N-(8-(2-hydroxybenzoyl)amino)caprylic acid is in the caprylic acid form and/or the caprylate form. In some embodiments the salt of N-(8-(2-hydroxybenzoyl)amino)caprylic acid comprises one monovalent cation, two monovalent cations or one divalent cation. In some embodiments the salt of N-(8-(2-hydroxybenzoyl) amino) caprylic acid is selected from the group consisting of the sodium salt, potassium salt and calcium salt of N-(8-(2-hydroxybenzoyl)amino)caprylic acid. Salts of N-(8-(2-hydroxybenzoyl)amino)caprylate may be prepared using the method described in e.g. WO96/030036, WO00/046182, WO01/092206 or WO2008/028859. The salt of N-(8-(2-hydroxybenzoyl)amino)caprylic acid may be crystalline and/or amorphous. In some embodiments the enhancer comprises the anhydrate, monohydrate, dihydrate, trihydrate, a solvate or one third of a hydrate of the salt of N-(8-(2-hydroxybenzoyl)amino) caprylic acid as well as combinations thereof. In some embodiments the enhancer is a salt of N-(8-(2-hydroxybenzoyl)amino)caprylic acid as described in WO2007/121318. In some embodiments the enhancer is sodium N-(8-(2-hydroxybenzoyl)amino)caprylate (referred to as "SNAC" herein), also known as sodium 8-(salicyloylamino) octanoate. In some embodiments the weight percentage of the salt of N-(8-(2-hydroxybenzoyl) amino)caprylic acid, such as SNAC, is at least 60% (w/w), such as at least 70% (w/w) or at least 75% (w/w), of the total weight of the composition. In some embodiments the weight percentage of the salt of N-(8-(2-hydroxybenzoyl)amino) caprylic acid, such as SNAC, is 50-90% (w/w) of the total weight of the composition. In some embodiments the amount of the salt of N-(8-(2-hydroxybenzoyl) amino) caprylic acid in the composition is in the range of 0.6-3.5 mmol. In some embodiments the amount of the salt of N-(8-(2-hydroxybenzoyl) amino)caprylic acid in the composition is at least 0.6 mmol. In some embodiments the amount of SNAC in the composition is in the range of 100-1000 mg. In some embodiments the amount of SNAC is 100-500 mg, such as 200-400 mg or 300 mg. In some embodiments the molar ratio between GLP-1 peptide and enhancer in the composition is less than 10, such as less than 5 or less than 1.

Composition

The method or use of the invention comprises a composition comprising a GLP-1 peptide and optionally an enhancer. In some embodiments the composition is in the form of a solid dosage form. In some embodiments the composition is in the form of a tablet. In some embodiments the composition is in the form of a capsule. In some embodiments the composition is in the form of a sachet. In some embodiments the composition comprises granules which have been manufactured by dry granulation. In some embodiments the composition comprises granules which have been manufactured by roller compaction. In some embodiments the moldings from the roller compaction process are comminuted into granules. In some embodiments the term "granulate" refers to one or more granules. In some embodiments the term "granule" refers to particles gathered into larger particles.

In some embodiments the term "composition" as used herein refers to one dosage unit.

In some embodiments the composition or granule comprises at least one pharmaceutically acceptable excipient. The term "excipient" as used herein broadly refers to any component other than the active therapeutic ingredient(s). The excipient may be an inert substance, which is inert in the sense that it substantially does not have any therapeutic and/or prophylactic effect per se. The excipient may serve various purposes, e.g. as a enhancer, absorption enhancer, vehicle, filler (also known as diluents), binder, lubricant, glidant, disintegrant, crystallization retarders, acidifying agent, alkalizing agent, preservative, antioxidant, buffering agent, chelating agent, complexing agents, surfactant agent, emulsifying and/or solubilizing agents, sweetening agents, wetting agents stabilizing agent, colouring agent, flavouring agent, and/or to improve administration, and/or absorption of the active substance. A person skilled in the art may select one or more of the aforementioned excipients with respect to the particular desired properties of the solid oral dosage form by routine experimentation and without any undue burden. The amount of each excipient used may vary within ranges conventional in the art. Techniques and excipients which may be used to formulate oral dosage forms are described in Handbook of Pharmaceutical Excipients, 6th edition, Rowe et al., Eds., American Pharmaceuticals Association and the Pharmaceutical Press, publications department of the Royal Pharmaceutical Society of Great Britain (2009); and Remington: the Science and Practice of Pharmacy, 21th edition, Gennaro, Ed., Lippincott Williams & Wilkins (2005).

In some embodiments the composition or granule comprises a filler, such as lactose (e.g. spray-dried lactose, α-lactose, β-lactose, Tabletose®, various grades of Pharmatose®, Microtose® or Fast-FloC®), microcrystalline cellulose (various grades of Avicel®, Elcema®, Vivacel®, Ming Tai® or Solka-Floc®), other cellulose derivatives, sucrose, sorbitol, mannitol, dextrins, dextrans, maltodextrins, dextrose, fructose, kaolin, mannitol, sorbitol, sucrose, sugar, starches or modified starches (including potato starch, maize starch and rice starch), calcium phosphate (e.g. basic calcium phosphate, calcium hydrogen phosphate, dicalcium phosphate hydrate), calcium sulphate, calcium carbonate, or sodium alginate. In some embodiments the filler is microcrystalline cellulose, such as Avicel PH 101.

In some embodiments the composition or granule comprises a binder, such as lactose (e.g. spray-dried lactose, α-lactose, β-lactose, Tabletose®, various grades of Pharmatose®, Microtose® or Fast-FloC®), microcrystalline cellulose (various grades of Avicel®, Elcema®, Vivacel®, Ming Tai® or Solka-Floc®), hydroxypropylcellulose, L-hydroxypropylcellulose (low-substituted), hypromellose (HPMC) (e.g. Methocel E, F and K, Metolose SH of Shin-Etsu, Ltd, such as, e.g., the 4,000 cps grades of Methocel E and Metolose 60 SH, the 4,000 cps grades of Methocel F and Metolose 65 SH, the 4,000, 15,000 and 100,000 cps grades of Methocel K; and the 4,000, 15,000, 39,000 and 100,000 grades of Metolose 90 SH), methylcellulose polymers (such as, e.g., Methocel A, Methocel A4C, Methocel A15C, Methocel A4M), hydroxyethylcellulose, ethylcellulose, sodium carboxymethylcellulose, other cellulose derivatives, sucrose, dextrins, maltodextrins, starches or modified starches (including potato starch, maize starch and rice starch), calcium lactate, calcium carbonate, acacia, sodium alginate, agar, carrageenan, gelatin, guar gum, pectin, PEG, or povidone. In some embodiments the binder is povidone, such as povidone K 90.

In some embodiments the composition or granule comprises a disintegrant, such as alginic acid, alginates, microcrystalline cellulose, hydroxypropyl cellulose, other cellulose derivatives, croscarmellose sodium, crospovidone, polacrillin potassium, sodium starch glycolate, starch, pregelatinized starch, or carboxymethyl starch (e.g. Primogel® and Explotab®).

In some embodiments the composition or granule comprises a lubricant, such as stearic acid, magnesium stearate, calcium stearate or other metallic stearate, talc, waxes, glycerides, light mineral oil, glyceryl behenate, hydrogenated vegetable oils, sodium stearyl fumarate, polyethylene glycols, alkyl sulfates, or sodium benzoate. In some embodiments the composition or granule comprises a lubricant, such as magnesium silicate, talc, or colloidal silica. In some embodiments the lubricant is magnesium stearate.

In some embodiments the composition or granule comprises one or more excipients selected from crystallization retarders, such as Povidone, etc.; solubilizing agents (also known as surfactants), such as anionic surfactants (e.g. Pluronic or Povidone), cationic surfactants, nonionic surfactants, and/or zwitterionic surfactants; colouring agents, including dyes and pigments, such as Iron Oxide Red or Yellow, titanium dioxide, and/or talc; and/or pH control agents, such as citric acid, tartaric acid, fumaric acid, sodium citrate, dibasic calcium phosphate, and/or dibasic sodium phosphate.

In some embodiments the composition comprises at least 60% (w/w) enhancer, less than 10% (w/w) binder, 5-40% (w/w) filler, and less than 10% (w/w) lubricant. In some embodiments the enhancer is a salt of N-(8-(2-hydroxybenzoyl)amino)caprylic acid and the composition comprises a first granule comprising GLP-1 peptide and no a salt of N-(8-(2-hydroxybenzoyl)amino)caprylic acid and a second granule comprising a salt of N-(8-(2-hydroxybenzoyl) amino)caprylic acid and no GLP-1 peptide.

In some embodiments the weight of the tablet is in the range of 150 mg to 1000 mg, such as in the range of 300-600 mg or such as 300-500 mg.

The composition may comprise one or more coatings, which may be prepared according to methods well known in the art.

Methods of Preparation of Compositions

The composition for use in the present invention may be prepared as is known in the art. In some embodiments the composition may be granulated prior to being compressed into tablets. In some embodiments the granules of the invention are manufactured by dry granulation, such as by roller compaction compaction. In some embodiments the moldings from the roller compactions process are comminuted into granules. The composition may comprise one or more intragranular parts and an extragranular part, wherein the intragranular parts have been granulated, and wherein the extragranular part has been added after granulation. A first intragranular part may comprise the GLP-1 peptide and one or more excipients, and a second intragranular part may comprise the enhancer and optionally one or more excipients. A first intragranular part may comprise the GLP-1 peptide, filler and/or a binder and a second intragranular part may comprise the enhancer, lubricant and/or filler. In some embodiments the first intragranular part comprises the GLP-1 peptide, microcrystalline cellulose and/or povidone and the second intragranular part comprises the enhancer, magnesium stearate and/or microcrystalline cellulose. The extragranular part may comprise a lubricant. In some embodiments the extragranular part comprises magnesium stearate.

To prepare a dry blend of tabletting material, the various components are weighed, optionally delumped and then combined. The mixing of the components may be carried out until a homogeneous blend is obtained.

In some embodiments at least a part of the composition is dry granulated or wet granulated. A granulate may be produced in a manner known to a person skilled in the art, for example by dry granulation techniques in which the pharmaceutically active agent and/or enhancers are compacted with the excipients to form relatively large moldings, for example slugs or ribbons, which are comminuted by grinding, and the ground material serves as the tabletting material to be later compressed into tablets. Suitable equipment for dry granulation includes but is not limited to roller compaction equipment from Gerteis, such as Gerteis MINI-PACTOR. In some embodiments the granulate is prepared by roller compaction. In some embodiments the moldings from the roller compactions process are comminuted into granules. Alternatively, a granulate can be obtained by wet granulation which may be carried out by mixing the pharmaceutically active agent dissolved in water with a dry blend of the enhancers and optionally one or more excipients followed by drying of the granulate.

To compress the tabletting material into a solid oral dosage form, for example a tablet, a tablet press may be used. In a tabletting press, the tabletting material is filled (e.g. force fed or gravity fed) into a die cavity. The tabletting material is then compressed by a punch with pressure. Subsequently, the resulting compact, or tablet is ejected from the tabletting press. The above mentioned compression process is subsequently referred to herein as the "compression process". Suitable tablet presses include, but are not limited to, rotary tablet presses and eccentric tablet presses. Examples of tablet presses include, but are not limited to, the Fette 102i (Fette GmbH), the Korsch XL100, the Korsch PH 106 rotary tablet press (Korsch AG, Germany), the Korsch EK-O eccentric tabletting press (Korsch AG, Germany) and the Manesty F-Press (Manesty Machines Ltd., United Kingdom). In some embodiments the tablet is prepared by exerting a compression force in the range of 5-25 kN.

Indications

The composition for use in the present invention is for use in as a medicament. In some embodiments the composition is for use in the treatment or prevention of diabetes and/or obesity.

It will be appreciated that the composition or the GLP-1 peptide for use as an oral pharmaceutical (i.e. medicament), may be described as a method of administration or alternatively be described as use of a composition in the manufacture of an oral pharmaceutical. It will be appreciated that the method of administration described herein may alternatively be described as a composition for use as an oral pharmaceutical, alternatively use of a composition in the manufacture of an oral pharmaceutical. The method of administration described herein may alternatively be described as a GLP-1 peptide for use as an oral pharmaceutical, alternatively use of a GLP-1 peptide in the manufacture of an oral pharmaceutical. Analogously, the use of a GLP-1 peptide described herein may alternatively be described as a method of administration or use of a GLP-1 peptide in the manufacture of an oral pharmaceutical. In some embodiments the terms "dosing regimen" and "method of administration" are used interchangeably herein. Herein, in some embodiments the term "use" includes a composition for use, e.g. "use in medicine" includes a "composition for use in medicine". In some embodiments the term "method" as used herein includes a method of administration, e.g. a method of oral administration.

The method of administration of the invention comprises oral therapy. In some embodiments the method comprises treatment or prevention of diabetes and/or obesity.

In some embodiments the method or use comprises (e.g. the GLP-1 peptide of the invention may be used for the following medical treatments):

(i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1c;

(ii) delaying or preventing diabetic disease progression, such as progression in type 2 diabetes, delaying the progression of impaired glucose tolerance (IGT) to insulin requiring type 2 diabetes, and/or delaying the progression of non-insulin requiring type 2 diabetes to insulin requiring type 2 diabetes;

(iii) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; and/or delaying gastric emptying.

In some embodiments the indication is (i). In some embodiments the indication is (ii). In a still further particular aspect the indication is (iii). In some embodiments the indication is type 2 diabetes and/or obesity.

In some embodiments the method or use comprises prevention, treatment, reduction and/or induction in one or more diseases or conditions defined herein. In some embodiments the indication is (i) and (iii). In some embodiments the indication is (ii) and (iii). In some embodiments the method comprises prevention, treatment, reduction and/or induction in one or more diseases or conditions selected from a) and b), a) and c), b) and c), or a), b) and c) as defined in claim 1.

In some embodiments the invention comprises administration of an effective amount of a GLP-1 peptide. In some embodiments the invention relates to administration of an effective amount of a GLP-1 peptide.

In some embodiments, as used herein, specific values given in relation to numbers or intervals may be understood as the specific value or as about the specific value.

EMBODIMENTS OF THE INVENTION

The following are non-limiting embodiments of the invention:

1. A solid composition comprising a GLP-1 peptide and an enhancer for use as a medicament by oral administration, wherein said peptide has plasma half-life in humans of at least 60 hours, wherein said composition is administered at least 3 times, and wherein a) said composition is administered every second day or more often; or b) said composition is administered such that the ratio between the plasma half-life in days in humans of said peptide and the dosing interval in days of said composition is more than 2:1.

2. The composition according to any one of the preceding embodiments, wherein said composition is in the form of a tablet.

3. The composition according to any one of the preceding embodiments, wherein said composition is administered twice daily, once daily, or every second day.

4. The composition according to any one of the preceding embodiments, wherein said peptide is administered at least every second day.

5. The composition according to any one of the preceding embodiments, wherein said peptide is administered at least once daily.

6. The composition according to any one of the preceding embodiments, wherein said peptide is administered at least twice daily.

7. The composition according to any one of the preceding embodiments, wherein said peptide is a GLP-1 peptide.

8. The composition according to any one of the preceding embodiments, wherein said peptide is an acylated GLP-1 peptide.

9. The composition according to any one of the preceding embodiments, wherein said peptide is N-epsilon26-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl][Aib8,Arg34]GLP-1-(7-37) or $N^{\epsilon 26}$\{2-[2-(2-\{2-[2-(2-\{(S)-4-Carboxy-4-[10-(4-carboxyphenoxy)decanoylamino]butyrylamino\}ethoxy)ethoxy]acetylamino\}ethoxy)ethoxy]acetyl\}, $N^{\epsilon 37}$-\{2-[2-(2-\{2-[2-(2-\{(S)-4-carboxy-4-[10-(4-carboxyphenoxy)decanoylamino]butyrylamino\}ethoxy)ethoxy]acetylamino\}ethoxy)ethoxy]acetyl\}-[Aib$^8$,Arg$^{34}$,Lys$^{37}$]GLP-1(7-37)-OH.

10. The composition according to any one of the preceding embodiments, wherein said peptide is N-epsilon26-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl][Aib8,Arg34]GLP-1-(7-37).

11. The composition according to any one of the preceding embodiments, wherein said peptide is $N^{\epsilon 26}$\{2-[2-(2-\{2-[2-(2-\{(S)-4-Carboxy-4-[10-(4-carboxyphenoxy)decanoylamino]butyrylamino\}-ethoxy)ethoxy]acetylamino\}ethoxy)ethoxy]acetyl\}, $N^{\epsilon 37}$-\{2-[2-(2-\{2-[2-(2-\{(S)-4-carboxy-4-[10-(4-carboxyphenoxy)decanoylamino]butyrylamino\}ethoxy)ethoxy]acetylamino\}ethoxy)ethoxy]acetyl\}-[Aib$^8$,Arg$^{34}$, Lys$^{37}$]GLP-1 (7-37)-OH.

12. The composition according to any one of the preceding embodiments, wherein said peptide is administered in a composition further comprising one or more pharmaceutically acceptable excipients.

13. The composition according to any one of the preceding embodiments, wherein said composition is in the form a tablet or a capsule.

14. The composition according to any one of the preceding embodiments, wherein said peptide is administered in a dosage which provides a steady state average plasma concentration of said peptide of 1-1000 nM.

15. A GLP-1 according to any one of the preceding embodiments, wherein said peptide is administered in a dosage which provides a steady state average plasma concentration of said peptide of 1-300 nM.

16. A GLP-1 according to any one of the preceding embodiments, wherein said peptide is administered in a dosage which provides a steady state average plasma concentration of said peptide of 10-100 nM.

17. The composition according to any one of the preceding embodiments, wherein said treatment comprises prevention and/or treatment of type 2 diabetes or obesity.

18. The composition according to any one of the preceding embodiments, wherein said enhancer is a salt of N-(8-(2-hydroxybenzoyl)amino)caprylic acid, such as SNAC.

19. The composition according to any one of the preceding embodiments, wherein the weight percentage of a salt of N-(8-(2-hydroxybenzoyl)amino)caprylic acid, such as SNAC, is at least 50% (w/w) of said composition.

20. The composition according to any one of the preceding embodiments, wherein the amount of SNAC is 100-500 mg SNAC, such as 200-400 mg or 300 mg SNAC.

21. The composition according to any one of the preceding embodiments, wherein said enhancer is a salt of capric acid, such as sodium caprate.

22. The composition according to any one of the preceding embodiments, wherein the amount of said salt of capric acid, such as sodium caprate, is at least 300 mg.

23. The composition according to any one of the preceding embodiments, wherein the weight percentage of said salt of capric acid, such as sodium caprate, is at least 50% (w/w) of said composition.

24. The composition according to any one of the preceding embodiments, wherein said composition comprises a coating.

25. The composition according to any one of the preceding embodiments, wherein said peptide has plasma half-life in humans of at least 70 hours.

26. The composition according to any one of the preceding embodiments, wherein said peptide is administered in an amount of 0.01-100 mg, such as 2-60 mg, or such as such as at least 5 mg or at least 10 mg.

27. The composition according to any one of the preceding embodiments, wherein said peptide is administered in an amount in the range of 0.5-100 mg.

28. The composition according to any one of the preceding embodiments, wherein said peptide is administered in an amount in the range of 0.5-50 mg.

29. The composition according to any one of the preceding embodiments, wherein said peptide is administered in an amount in the range of 0.5-25 mg.

30. The composition according to any one of the preceding embodiments, wherein said peptide is administered in an amount in the range of 1-25 mg.

31. The composition according to any one of the preceding embodiments, wherein said peptide is administered in an amount in the range of 5-50 mg.

32. The composition according to any one of the preceding embodiments, wherein said peptide is administered in an amount in the range of 0.5-10 mg.

33. The composition according to any one of the preceding embodiments, wherein said peptide is administered in an amount in the range of 0.5-5 mg.

34. The composition according to any one of the preceding embodiments, wherein said composition comprises 1-100 mg GLP-1 peptide and 100-500 mg or 50-90% (w/w) SNAC.

35. The composition according to any one of the preceding embodiments, wherein said peptide is semaglutide.

36. The composition according to any one of the preceding embodiments, wherein said composition comprises 1-100 mg semaglutide and 100-500 mg or 50-90% (w/w) SNAC.

37. The composition according to any one of the preceding embodiments, wherein said composition comprises 2-40 mg semaglutide and 200-400 mg (such as 300 mg) or 50-90% (w/w) SNAC.

38. The composition according to any one of the preceding embodiments, wherein said peptide is comprised in a pharmaceutical composition further comprising one or more pharmaceutically acceptable excipients.

39. The composition according to any one of the preceding embodiments, wherein said composition comprises GLP-1 peptide, SNAC, microcrystalline cellulose, povidone, and magnesium stearate.

40. The composition according to any one of the preceding embodiments, wherein said composition comprises 1-100 mg GLP-1 peptide, 100-500 mg SNAC, microcrystalline cellulose, povidone, and magnesium stearate.

41. The composition according to any one of the preceding embodiments, wherein said composition comprises 1-100 mg GLP-1 peptide, 50-90% (w/w) SNAC, microcrystalline cellulose, povidone, and magnesium stearate.

44. The composition according to any one of the preceding embodiments, wherein said composition contains 1-100 mg GLP-1 peptide, 100-500 mg or 50-90% (w/w) SNAC, microcrystalline cellulose, povidone, and magnesium stearate.

45. The composition according to any one of the preceding embodiments, wherein said composition contains 1-100 mg GLP-1 peptide, 100-500 mg or 50-90% (w/w) SNAC, microcrystalline cellulose, povidone, and magnesium stearate.

46. The composition according to any one of the preceding embodiments, wherein said composition contains 1-100 mg GLP-1 peptide, 200-400 mg (such as 300 mg) or 50-90% (w/w) SNAC, microcrystalline cellulose, povidone, and magnesium stearate.

47. The composition according to any one of the preceding embodiments, wherein said composition contains 1-100 mg semaglutide, 200-400 mg (such as 300 mg) or 50-90% (w/w) SNAC, microcrystalline cellulose, povidone, and magnesium stearate.

48. The composition according to any one of the preceding embodiments, wherein said composition contains 2-60 mg semaglutide, 200-400 mg (such as 300 mg) or 50-90% (w/w) SNAC, microcrystalline cellulose, povidone, and magnesium stearate.

49. The composition according to any one of the preceding embodiments, wherein said composition contains 5-40 mg semaglutide, 200-400 mg (such as 300 mg) or 50-90% (w/w) SNAC, microcrystalline cellulose, povidone, and magnesium stearate.

50. The composition according to any one of the preceding embodiments, wherein said composition is administered at least 5 times, such as at least 7 times or at least 10 times.

51. The composition according to any one of the preceding embodiments, wherein said composition is administered at least 14 times or at least 21 times.

52. The composition according to any one of the preceding embodiments, wherein said composition is administered for at least 2 weeks, for at least 3 weeks, or for at least 4 weeks.

53. The composition according to any one of the preceding embodiments, wherein the ratio between the plasma half-life in days in humans of said peptide and the dosing interval in days of said peptide is more than 3:1.

54. The composition according to any one of the preceding embodiments, wherein the ratio between the plasma half-life in days in humans of said peptide and the dosing interval in days of said peptide is more than 4:1.

55. The composition according to any one of the preceding embodiments, wherein the ratio between the plasma half-life in days in humans of said peptide and the dosing interval in days of said peptide is more than 5:1.

56. The composition according to any one of the preceding embodiments, wherein the ratio between the plasma half-life in days in humans of said peptide and the dosing interval in days of said peptide is more than 6:1.

57. The composition according to any one of the preceding embodiments, wherein the ratio between the plasma half-life in days in humans of said peptide and the dosing interval in days of said peptide is more than 7:1.

58. The composition according to any one of the preceding embodiments, wherein the ratio between the plasma half-life in days in humans of said peptide and the dosing interval in days of said peptide is more than 14:1.

59. The composition according to any one of the preceding embodiments, wherein plasma half-life is measured after i.v. administration.

60. The composition according to any one of the preceding embodiments, wherein plasma half-life is measured after p.o. administration.

61. The composition according to any one of the preceding embodiments, wherein said composition is for use in the treatment or prevention of diabetes and/or obesity.

62. The composition according to any one of the preceding embodiments, wherein said composition is for use in the following medical treatments:

(i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1c;

(ii) delaying or preventing diabetic disease progression, such as progression in type 2 diabetes, delaying the progression of impaired glucose tolerance (IGT) to insulin requiring type 2 diabetes, and/or delaying the progression of non-insulin requiring type 2 diabetes to insulin requiring type 2 diabetes; and/or (iii) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; and/or delaying gastric emptying.

63. A method of oral administration of a pharmaceutically active GLP-1 peptide to a subject, wherein said peptide has plasma half-life in humans of at least 60 hours, and wherein said method comprises the step of administering said peptide every second day or more often in a therapeutically effective amount.

64. A method of oral administration of a solid composition comprising a GLP-1 peptide and an enhancer to a subject in need thereof, wherein said peptide has plasma half-life in humans of at least 60 hours, wherein said composition is administered at least 3 times, and wherein a) said composition is administered every second day or more often; or b) said composition is administered such that the ratio between the plasma half-life in days in humans of said peptide and the dosing interval in days of said composition is more than 2:1.

65. A method of oral administration of a solid composition comprising a GLP-1 peptide and an enhancer to a subject in need thereof, wherein said peptide has plasma half-life in humans of at least 60 hours, wherein said composition is administered at least 3 times, and wherein said composition is administered every second day or more often.

66. A method of oral administration of a solid composition comprising a GLP-1 peptide and an enhancer to a subject in need thereof, wherein said peptide has plasma half-life in humans of at least 60 hours, wherein said composition is administered at least 3 times, and wherein said composition is administered such that the ratio between the plasma half-life in days in humans of said peptide and the dosing interval in days of said composition is more than 2:1.

67. The method according to any one of the preceding embodiments, wherein said composition is in the form of a tablet.

68. The method according to any one of the preceding embodiments, wherein said composition is administered twice daily, once daily, or every second day.

69. The method according to any one of the preceding embodiments, wherein said peptide is administered at least every second day.

70. The method according to any one of the preceding embodiments, wherein said peptide is administered at least once daily.

71. The method according to any one of the preceding embodiments, wherein said peptide is administered at least twice daily.

72. The method according to any one of the preceding embodiments, wherein said peptide is a GLP-1 peptide.

73. The method according to any one of the preceding embodiments, wherein said peptide is an acylated GLP-1 peptide.

74. The method according to any one of the preceding embodiments, wherein said peptide is N-epsilon26-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl][Aib8,Arg34]GLP-1-(7-37) or $N^{\varepsilon 26}$\{2-[2-(2-{2-[2-(2-{(S)-4-Carboxy-4-[10-(4-carboxyphenoxy)decanoylamino]butyrylamino}ethoxy)ethoxy]-acetylamino}ethoxy)ethoxy]acetyl\}, $N^{\varepsilon 37}$-\{2-[2-(2-{2-[2-(2-{(S)-4-carboxy-4-[10-(4-carboxy- phenoxy)decanoylamino]butyrylamino}ethoxy)ethoxy]acetylamino}ethoxy)ethoxy]acetyl\}-[Aib$^8$,Arg$^{34}$, Lys$^{37}$] GLP-1 (7-37)-OH.

75. The method according to any one of the preceding embodiments, wherein said peptide is N-epsilon26-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl][Aib8,Arg34]GLP-1-(7-37).

11. The method according to any one of the preceding embodiments, wherein said peptide is $N^{\varepsilon 26}$\{2-[2-(2-{2-[2-(2-{(S)-4-Carboxy-4-[10-(4-carboxyphenoxy)decanoylamino]butyrylamino}ethoxy)ethoxy]acetylamino}ethoxy)ethoxy]acetyl\}, $N^{\varepsilon 37}$-\{2-[2-(2-{2-[2-(2-{(S)-4-carboxy-4-[10-(4-carboxyphenoxy)decanoylamino]butyrylamino}ethoxy)ethoxy]acetylamino}ethoxy)ethoxy]acetyl\}-[Aib$^8$,Arg$^{34}$, Lys$^{37}$]GLP-1 (7-37)-OH.

76. The method according to any one of the preceding embodiments, wherein said peptide is administered in a composition further comprising one or more pharmaceutically acceptable excipients.

77. The method according to any one of the preceding embodiments, wherein said composition is in the form a tablet or a capsule.

78. The method according to any one of the preceding embodiments, wherein said peptide is administered in a dosage which provides a steady state average plasma concentration of said peptide of 1-1000 nM.

79. A GLP-1 according to any one of the preceding embodiments, wherein said peptide is administered in a dosage which provides a steady state average plasma concentration of said peptide of 1-300 nM.

80. A GLP-1 according to any one of the preceding embodiments, wherein said peptide is administered in a dosage which provides a steady state average plasma concentration of said peptide of 10-100 nM.

81. The method according to any one of the preceding embodiments, wherein said treatment comprises prevention and/or treatment of type 2 diabetes or obesity.

82. The method according to any one of the preceding embodiments, wherein said enhancer is a salt of N-(8-(2-hydroxybenzoyl)amino)caprylic acid, such as SNAC.

83. The method according to any one of the preceding embodiments, wherein the weight percentage of a salt of N-(8-(2-hydroxybenzoyl)amino)caprylic acid, such as SNAC, is at least 50% (w/w) of said composition.

84. The method according to any one of the preceding embodiments, wherein the amount of SNAC is 100-500 mg SNAC, such as 200-400 mg or 300 mg SNAC.

85. The method according to any one of the preceding embodiments, wherein said enhancer is a salt of capric acid, such as sodium caprate.

86. The method according to any one of the preceding embodiments, wherein the amount of said salt of capric acid, such as sodium caprate, is at least 300 mg.

87. The method according to any one of the preceding embodiments, wherein the weight percentage of said salt of capric acid, such as sodium caprate, is at least 50% (w/w) of said composition.

88. The method according to any one of the preceding embodiments, wherein said composition comprises a coating.

89. The method according to any one of the preceding embodiments, wherein said peptide has plasma half-life in humans of at least 70 hours.

90. The method according to any one of the preceding embodiments, wherein said peptide is administered in an amount of 0.01-100 mg, such as 2-60 mg, or such as such as at least 5 mg or at least 10 mg.

91. The method according to any one of the preceding embodiments, wherein said peptide is administered in an amount in the range of 0.5-100 mg.

92. The method according to any one of the preceding embodiments, wherein said peptide is administered in an amount in the range of 0.5-50 mg.

93. The method according to any one of the preceding embodiments, wherein said peptide is administered in an amount in the range of 0.5-25 mg.

94. The method according to any one of the preceding embodiments, wherein said peptide is administered in an amount in the range of 1-25 mg.

95. The method according to any one of the preceding embodiments, wherein said peptide is administered in an amount in the range of 5-50 mg.

96. The method according to any one of the preceding embodiments, wherein said peptide is administered in an amount in the range of 0.5-10 mg.

97. The method according to any one of the preceding embodiments, wherein said peptide is administered in an amount in the range of 0.5-5 mg.

98. The method according to any one of the preceding embodiments, wherein said composition comprises 1-100 mg GLP-1 peptide and 100-500 mg or 50-90% (w/w) SNAC.

99. The method according to any one of the preceding embodiments, wherein said peptide is semaglutide.

100. The method according to any one of the preceding embodiments, wherein said composition comprises 1-100 mg semaglutide and 100-500 mg or 50-90% (w/w) SNAC.

101. The method according to any one of the preceding embodiments, wherein said composition comprises 2-40 mg semaglutide and 200-400 mg (such as 300 mg) or 50-90% (w/w) SNAC.

102. The method according to any one of the preceding embodiments, wherein said peptide is comprised in a pharmaceutical composition further comprising one or more pharmaceutically acceptable excipients.

103. The method according to any one of the preceding embodiments, wherein said composition comprises GLP-1 peptide, SNAC, microcrystalline cellulose, povidone, and magnesium stearate.

104. The method according to any one of the preceding embodiments, wherein said composition comprises 1-100 mg GLP-1 peptide, 100-500 mg SNAC, microcrystalline cellulose, povidone, and magnesium stearate.

105. The method according to any one of the preceding embodiments, wherein said composition comprises 1-100 mg GLP-1 peptide, 50-90% (w/w) SNAC, microcrystalline cellulose, povidone, and magnesium stearate.

106. The method according to any one of the preceding embodiments, wherein said composition contains 1-100 mg GLP-1 peptide, 100-500 mg or 50-90% (w/w) SNAC, microcrystalline cellulose, povidone, and magnesium stearate.

107. The method according to any one of the preceding embodiments, wherein said composition contains 1-100 mg GLP-1 peptide, 100-500 mg or 50-90% (w/w) SNAC, microcrystalline cellulose, povidone, and magnesium stearate.

108. The method according to any one of the preceding embodiments, wherein said composition contains 1-100 mg GLP-1 peptide, 200-400 mg (such as 300 mg) or 50-90% (w/w) SNAC, microcrystalline cellulose, povidone, and magnesium stearate.

109. The method according to any one of the preceding embodiments, wherein said composition contains 1-100 mg semaglutide, 200-400 mg (such as 300 mg) or 50-90% (w/w) SNAC, microcrystalline cellulose, povidone, and magnesium stearate.

110. The method according to any one of the preceding embodiments, wherein said composition contains 2-60 mg semaglutide, 200-400 mg (such as 300 mg) or 50-90% (w/w) SNAC, microcrystalline cellulose, povidone, and magnesium stearate.

111. The method according to any one of the preceding embodiments, wherein said composition contains 5-40 mg semaglutide, 200-400 mg (such as 300 mg) or 50-90% (w/w) SNAC, microcrystalline cellulose, povidone, and magnesium stearate.

112. The method according to any one of the preceding embodiments, wherein said composition is administered at least 5 times, such as at least 7 times or at least 10 times.

113. The method according to any one of the preceding embodiments, wherein said composition is administered at least 14 times or at least 21 times.

114. The method according to any one of the preceding embodiments, wherein said composition is administered for at least 2 weeks, for at least 3 weeks, or for at least 4 weeks.

115. The method according to any one of the preceding embodiments, wherein the ratio between the plasma half-life in days in humans of said peptide and the dosing interval in days of said peptide is more than 3:1.

116. The method according to any one of the preceding embodiments, wherein the ratio between the plasma half-life in days in humans of said peptide and the dosing interval in days of said peptide is more than 4:1.

117. The method according to any one of the preceding embodiments, wherein the ratio between the plasma half-life in days in humans of said peptide and the dosing interval in days of said peptide is more than 5:1.

118. The method according to any one of the preceding embodiments, wherein the ratio between the plasma half-life in days in humans of said peptide and the dosing interval in days of said peptide is more than 6:1.

119. The method according to any one of the preceding embodiments, wherein the ratio between the plasma half-life in days in humans of said peptide and the dosing interval in days of said peptide is more than 7:1.

120. The method according to any one of the preceding embodiments, wherein the ratio between the plasma half-life in days in humans of said peptide and the dosing interval in days of said peptide is more than 14:1.

121. The method according to any one of the preceding embodiments, wherein plasma half-life is measured after i.v. administration.

122. The method according to any one of the preceding embodiments, wherein plasma half-life is measured after p.o. administration.

123. The method according to any one of the preceding embodiments, wherein said composition is for use in the treatment or prevention of diabetes and/or obesity.

124. The method according to any one of the preceding embodiments, wherein said composition is for use in the following medical treatments:
(i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1c;
(ii) delaying or preventing diabetic disease progression, such as progression in type 2 diabetes, delaying the progression of impaired glucose tolerance (IGT) to insulin requiring type 2 diabetes, and/or delaying the progression of non-insulin requiring type 2 diabetes to insulin requiring type 2 diabetes; and/or
(iii) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; and/or delaying gastric emptying.

125. Use of a GLP-1 peptide in the manufacture of a medicament for oral administration in the treatment of a disease or condition, such as diabetes, wherein said peptide has plasma half-life in humans of at least 60 hours, wherein said composition is administered at least 3 times, and a) said composition is administered every second day or more often; or b) said composition is administered such that the ratio between the plasma half-life in days in humans of said peptide and the dosing interval in days of said composition is more than 2:1.

126. Use of a solid composition comprising a GLP-1 peptide and an enhancer in the manufacture of a medicament for oral administration in the treatment of a disease or condition, such as diabetes, wherein said peptide has plasma half-life in humans of at least 60 hours, wherein said composition is administered at least 3 times, and wherein said composition is administered every second day or more often.

127. Use of a solid composition comprising a GLP-1 peptide and an enhancer in the manufacture of a medicament for oral administration in the treatment of a disease or condition, such as diabetes, wherein said peptide has plasma half-life in humans of at least 60 hours, wherein said composition is administered at least 3 times, and wherein said composition is administered such that the ratio between the plasma half-life in days in humans of said peptide and the dosing interval in days of said composition is more than 2:1.
128. The use according to any one of embodiments 125-127, wherein said GLP-1 peptide and/or said composition is as defined in any combination of the previous embodiments.

Further Particular Embodiments

The following are particular non-limiting embodiments of the invention:

1. A GLP-1 peptide for use as an oral pharmaceutical every second day or more often in medical treatment, wherein said peptide has plasma half-life in humans of at least 60 hours.
2. A GLP-1 peptide which is a low clearance GLP-1 peptide for use as an oral pharmaceutical in medical treatment, wherein dosing regimen is such that the ratio between the plasma half-life in days in humans of said peptide and the dosing interval in days of said peptide is more than 2:1.
3. A GLP-1 peptide according to any one of the preceding embodiments, wherein the ratio between the plasma half-life in days in humans of said peptide and the dosing interval in days of said peptide is more than 3:1.
4. A GLP-1 peptide according to any one of the preceding embodiments, wherein the ratio between the plasma half-life in days in humans of said peptide and the dosing interval in days of said peptide is more than 4:1.
5. A GLP-1 peptide according to any one of the preceding embodiments, wherein the ratio between the plasma half-life in days in humans of said peptide and the dosing interval in days of said peptide is more than 5:1.
6. A GLP-1 peptide according to any one of the preceding embodiments, wherein the ratio between the plasma half-life in days in humans of said peptide and the dosing interval in days of said peptide is more than 6:1.
7. A GLP-1 peptide according to any one of the preceding embodiments, wherein the ratio between the plasma half-life in days in humans of said peptide and the dosing interval in days of said peptide is more than 7:1.
8. A GLP-1 peptide according to any one of the preceding embodiments, wherein the ratio between the plasma half-life in days in humans of said peptide and the dosing interval in days of said peptide is more than 14:1.
9. A GLP-1 peptide according to any one of the preceding embodiments, wherein plasma half-life is measured after i.v. administration.
10. A GLP-1 peptide according to any one of the preceding embodiments, wherein plasma half-life is measured after p.o. administration.
11. A GLP-1 peptide according to any one of the preceding embodiments, wherein said peptide has plasma half-life in humans of at least 1 day.
12. A GLP-1 peptide according to any one of the preceding embodiments, wherein said peptide has plasma half-life in humans of at least 36 hours.
13. A GLP-1 peptide according to any one of the preceding embodiments, wherein said peptide has plasma half-life in humans of at least 2 days.
14. A GLP-1 peptide according to any one of the preceding embodiments, wherein said peptide has plasma half-life in humans of at least 60 hours.
15. A GLP-1 peptide according to any one of the preceding embodiments, wherein said peptide is administered at least every second day.
16. A GLP-1 peptide according to any one of the preceding embodiments, wherein said peptide is administered at least once daily.
17. A GLP-1 peptide according to any one of the preceding embodiments, wherein said peptide is administered at least twice daily.
18. A GLP-1 peptide according to any one of the preceding embodiments, wherein said peptide is administered in an amount in the range of 0.5-100 mg.
19. A GLP-1 peptide according to any one of the preceding embodiments, wherein said peptide is administered in an amount in the range of 0.5-50 mg.
20. A GLP-1 peptide according to any one of the preceding embodiments, wherein said peptide is administered in an amount in the range of 0.5-25 mg.
21. A GLP-1 peptide according to any one of the preceding embodiments, wherein said peptide is administered in an amount in the range of 1-25 mg.
22. A GLP-1 peptide according to any one of the preceding embodiments, wherein said peptide is administered in an amount in the range of 5-50 mg.
23. A GLP-1 peptide according to any one of the preceding embodiments, wherein said peptide is administered in an amount in the range of 0.5-10 mg.
24. A GLP-1 peptide according to any one of the preceding embodiments, wherein said peptide is administered in an amount in the range of 0.5-5 mg.
25. A GLP-1 peptide according to any one of the preceding embodiments, wherein said peptide is a GLP-1 peptide.
26. A GLP-1 peptide according to any one of the preceding embodiments, wherein said peptide is an acylated GLP-1 peptide.
27. A GLP-1 peptide according to any one of the preceding embodiments, wherein said peptide is N-epsilon26-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl][Aib8,Arg34]GLP-1-(7-37) or $N^{\varepsilon 26}$ {2-[2-(2-{2-[2-(2-{(S)-4-Carboxy-4-[10-(4-carboxyphenoxy)decanoylamino]butyrylamino}ethoxy)ethoxy]-acetylamino}ethoxy)ethoxy]acetyl}, $N^{\varepsilon 37}$-{2-[2-(2-{2-[2-(2-{(S)-4-carboxy-4-[10-(4-carboxy- phenoxy) decanoylamino]butyrylamino}ethoxy)ethoxy] acetylamino}ethoxy)ethoxy]acetyl}-[Aib$^8$,Arg$^{34}$, Lys$^{37}$] GLP-1 (7-37)-OH.
28. A GLP-1 peptide according to any one of the preceding embodiments, wherein said peptide is N-epsilon26-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl][Aib8,Arg34]GLP-1-(7-37).
29. A GLP-1 peptide according to any one of the preceding embodiments, wherein said peptide is $N^{\varepsilon 26}$ {2-[2-(2-{2-[2-(2-{(S)-4-Carboxy-4-[10-(4-carboxyphenoxy)decanoylamino]butyrylamino}-ethoxy)ethoxy]acetylamino}ethoxy)ethoxy]acetyl}, $N^{\varepsilon 37}$-{2-[2-(2-{2-[2-(2-{(S)-4-carboxy-4-[10-(4-carboxyphenoxy)decanoylamino]butyrylamino}ethoxy)ethoxy]acetylamino}ethoxy)ethoxy]acetyl}-[Aib$^8$,Arg$^{34}$, Lys$^{37}$]GLP-1 (7-37)-OH.
30. A GLP-1 peptide according to any one of the preceding embodiments, wherein said peptide is administered in a composition further comprising one or more pharmaceutically acceptable excipients.
31. A GLP-1 peptide according to embodiment 22, wherein said composition is in the form of a solid dosage form, such as a tablet or a capsule.
32. A GLP-1 peptide according to any one of the preceding embodiments, wherein said peptide is administered in a dosage which provides a steady state average plasma concentration of said peptide of 1-1000 nM.
33. A GLP-1 according to any one of the preceding embodiments, wherein said peptide is administered in a dosage which provides a steady state average plasma concentration of said peptide of 1-300 nM.

34. A GLP-1 according to any one of the preceding embodiments, wherein said peptide is administered in a dosage which provides a steady state average plasma concentration of said peptide of 10-100 nM.

35. A GLP-1 peptide according to any one of the preceding embodiments, wherein said treatment comprises prevention and/or treatment of type 2 diabetes or obesity.

36. A method of oral administration of a pharmaceutically active GLP-1 peptide to a subject, wherein said peptide has plasma half-life in humans of at least 60 hours, and wherein said method comprises the step of administering said peptide every second day or more often in a therapeutically effective amount.

37. A method of oral administration of a low clearance GLP-1 peptide in a therapeutically effective dosage to a subject, wherein the ratio between the plasma half-life in days in humans of said peptide and the dosing interval in days of said peptide is more than 2:1.

38. A method according to any one of the preceding embodiments, wherein the ratio between the plasma half-life in days in humans of said peptide and the dosing interval in days of said peptide is more than 3:1.

39. A method according to any one of the preceding embodiments, wherein the ratio between the plasma half-life in days in humans of said peptide and the dosing interval in days of said peptide is more than 4:1.

40. A method according to any one of the preceding embodiments, wherein the ratio between the plasma half-life in days in humans of said peptide and the dosing interval in days of said peptide is more than 5:1.

41. A method according to any one of the preceding embodiments, wherein the ratio between the plasma half-life in days in humans of said peptide and the dosing interval in days of said peptide is more than 6:1.

42. A method according to any one of the preceding embodiments, wherein the ratio between the plasma half-life in days in humans of said peptide and the dosing interval in days of said peptide is more than 7:1.

43. A method according to any one of the preceding embodiments, wherein the ratio between the plasma half-life in days in humans of said peptide and the dosing interval in days of said peptide is more than 14:1.

44. A method according to any one of the preceding embodiments, wherein plasma half-life is measured after i.v. administration.

45. A method according to any one of the preceding embodiments, wherein plasma half-life is measured after p.o. administration.

46. A method according to any one of the preceding embodiments, wherein said peptide has plasma half-life in humans of at least 1 day.

47. A method according to any one of the preceding embodiments, wherein said peptide has plasma half-life in humans of at least 36 hours.

48. A method according to any one of the preceding embodiments, wherein said peptide has plasma half-life in humans of at least 2 days.

49. A method according to any one of the preceding embodiments, wherein said peptide has plasma half-life in humans of at least 60 hours.

50. A method according to any one of the preceding embodiments, wherein said peptide is administered at least every second day.

51. A method according to any one of the preceding embodiments, wherein said peptide is administered at least once daily.

52. A method according to any one of the preceding embodiments, wherein said peptide is administered at least twice daily.

53. A method according to any one of the preceding embodiments, wherein said peptide is administered in an amount in the range of 0.5-100 mg.

54. A method according to any one of the preceding embodiments, wherein said peptide is administered in an amount in the range of 0.5-50 mg.

55. A method according to any one of the preceding embodiments, wherein said peptide is administered in an amount in the range of 0.5-25 mg.

56. A method according to any one of the preceding embodiments, wherein said peptide is administered in an amount in the range of 1-25 mg.

57 A method according to any one of the preceding embodiments, wherein said peptide is administered in an amount in the range of 5-50 mg.

58. A method according to any one of the preceding embodiments, wherein said peptide is administered in an amount in the range of 0.5-10 mg.

59. A method according to any one of the preceding embodiments, wherein said peptide is administered in an amount in the range of 0.5-5 mg.

60. A method according to any one of the preceding embodiments, wherein said peptide is a GLP-1 peptide.

61 A method according to any one of the preceding embodiments, wherein said peptide is an acylated GLP-1 peptide.

62. A method according to any one of the preceding embodiments, wherein said peptide is N-epsilon26-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl][Aib8,Arg34]GLP-1-(7-37) or $N^{\varepsilon 26}${2-[2-(2-{2-[2-(2-{(S)-4-Carboxy-4-[10-(4-carboxyphenoxy)decanoylamino]butyrylamino}ethoxy)ethoxy]-acetylamino}ethoxy)ethoxy]acetyl}, $N^{\varepsilon 37}$-{2-[2-(2-{2-[2-(2-{(S)-4-carboxy-4-[10-(4-carboxy-phenoxy)decanoylamino]butyrylamino}ethoxy)ethoxy]acetylamino}ethoxy)ethoxy]acetyl}-[$Aib^8$,$Arg^{34}$, $Lys^{37}$]GLP-1 (7-37)-OH.

63. A method according to any one of the preceding embodiments, wherein said peptide is N-epsilon26-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl][Aib8,Arg34]GLP-1-(7-37).

64. A method according to any one of the preceding embodiments, wherein said peptide is $N^{\varepsilon 26}${2-[2-(2-{2-[2-(2-{(S)-4-Carboxy-4-[10-(4-carboxyphenoxy)decanoylamino]butyrylamino}-ethoxy)ethoxy]acetylamino}ethoxy)ethoxy]acetyl}, $N^{\varepsilon 37}$-{2-[2-(2-{2-[2-(2-{(S)-4-carboxy-4-[10-(4-carboxyphenoxy)decanoylamino]butyrylamino}ethoxy)ethoxy]acetylamino}ethoxy)ethoxy]acetyl}-[$Aib^8$,$Arg^{34}$, $Lys^{37}$]GLP-1 (7-37)-OH.

65. A method according to any one of the preceding embodiments, wherein said peptide is administered in a composition further comprising one or more pharmaceutically acceptable excipients.

66. A method according to embodiment 22, wherein said composition is in the form of a solid dosage form, such as a tablet or a capsule.

67. A method according to any one of the preceding embodiments, wherein said peptide is administered in a dosage which provides a steady state average plasma concentration of said peptide of 1-1000 nM.

68. A method according to any one of the preceding embodiments, wherein said peptide is administered in a dosage which provides a steady state average plasma concentration of said peptide of 1-300 nM.

69. A method according to any one of the preceding embodiments, wherein said peptide is administered in a dosage which provides a steady state average plasma concentration of said peptide of 10-100 nM 70. A method according to any one of the preceding embodiments, wherein said method comprises prevention and/or treatment of type 2 diabetes or obesity.

71. Use of a GLP-1 peptide in the manufacture of a medicament for oral administration in the treatment of diabetes, wherein said peptide has plasma half-life in humans of at least 60 hours, and wherein said method comprises the step of administering said peptide every second day or more often in a therapeutically effective amount.

72. Use of a low clearance GLP-1 peptide in the manufacture of a medicament for oral administration in the treatment of diabetes, wherein the ratio between the plasma half-life in days in humans of said peptide and the dosing interval in days of said peptide is more than 2:1.

73. Use according to any one of the preceding embodiments, wherein the ratio between the plasma half-life in days in humans of said peptide and the dosing interval in days of said peptide is more than 3:1.

74. Use according to any one of the preceding embodiments, wherein the ratio between the plasma half-life in days in humans of said peptide and the dosing interval in days of said peptide is more than 4:1.

75. Use according to any one of the preceding embodiments, wherein the ratio between the plasma half-life in days in humans of said peptide and the dosing interval in days of said peptide is more than 5:1.

76. Use according to any one of the preceding embodiments, wherein the ratio between the plasma half-life in days in humans of said peptide and the dosing interval in days of said peptide is more than 6:1.

77. Use according to any one of the preceding embodiments, wherein the ratio between the plasma half-life in days in humans of said peptide and the dosing interval in days of said peptide is more than 7:1.

78. Use according to any one of the preceding embodiments, wherein the ratio between the plasma half-life in days in humans of said peptide and the dosing interval in days of said peptide is more than 14:1.

79. Use according to any one of the preceding embodiments, wherein plasma half-life is measured after i.v. administration.

80. Use according to any one of the preceding embodiments, wherein plasma half-life is measured after p.o. administration.

81. Use according to any one of the preceding embodiments, wherein said peptide has plasma half-life in humans of at least 1 day.

82. Use according to any one of the preceding embodiments, wherein said peptide has plasma half-life in humans of at least 36 hours.

83. Use according to any one of the preceding embodiments, wherein said peptide has plasma half-life in humans of at least 2 days.

84. Use according to any one of the preceding embodiments, wherein said peptide has plasma half-life in humans of at least 60 hours.

85. Use according to any one of the preceding embodiments, wherein said peptide is administered at least every second day.

86. Use according to any one of the preceding embodiments, wherein said peptide is administered at least once daily.

87. Use according to any one of the preceding embodiments, wherein said peptide is administered at least twice daily.

88. Use according to any one of the preceding embodiments, wherein said peptide is administered in an amount in the range of 0.5-100 mg.

89. Use according to any one of the preceding embodiments, wherein said peptide is administered in an amount in the range of 0.5-50 mg.

90. Use according to any one of the preceding embodiments, wherein said peptide is administered in an amount in the range of 0.5-25 mg.

91. Use according to any one of the preceding embodiments, wherein said peptide is administered in an amount in the range of 1-25 mg.

92. Use according to any one of the preceding embodiments, wherein said peptide is administered in an amount in the range of 5-50 mg.

93. Use according to any one of the preceding embodiments, wherein said peptide is administered in an amount in the range of 0.5-10 mg.

94. Use according to any one of the preceding embodiments, wherein said peptide is administered in an amount in the range of 0.5-5 mg.

95. Use according to any one of the preceding embodiments, wherein said peptide is a GLP-1 peptide.

96. Use according to any one of the preceding embodiments, wherein said peptide is an acylated GLP-1 peptide.

97. Use according to any one of the preceding embodiments, wherein said peptide is N-epsilon26-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl][Aib8,Arg34]GLP-1-(7-37) or $N^{\varepsilon 26}$\{2-[2-(2-\{2-[2-(2-\{(S)-4-Carboxy-4-[10-(4-carboxyphenoxy)decanoylamino]butyrylamino\}ethoxy)ethoxy]-acetylamino\}ethoxy)ethoxy]acetyl\}, $N^{\varepsilon 37}$-\{2-[2-(2-\{2-[2-(2-\{(S)-4-carboxy-4-[10-(4-carboxy- phenoxy)decanoylamino]butyrylamino\}ethoxy)ethoxy]acetylamino\}ethoxy)ethoxy]acetyl\}-[Aib$^8$,Arg$^{34}$,Lys$^{37}$]GLP-1 (7-37)-OH.

98. Use according to any one of the preceding embodiments, wherein said peptide is N-epsilon26-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl][Aib8,Arg34]GLP-1-(7-37).

99. A method according to any one of the preceding embodiments, wherein said peptide is $N^{\varepsilon 26}$\{2-[2-(2-\{2-[2-(2-\{(S)-4-Carboxy-4-[10-(4-carboxyphenoxy)decanoylamino]butyrylamino\}-ethoxy)ethoxy]acetylamino\}ethoxy)ethoxy]acetyl\}, $N^{\varepsilon 37}$-\{2-[2-(2-\{2-[2-(2-\{(S)-4-carboxy-4-[10-(4-carboxyphenoxy)decanoylamino]butyrylamino\}ethoxy)ethoxy]acetylamino\}ethoxy)ethoxy]acetyl\}-[Aib$^8$,Arg$^{34}$,Lys$^{37}$]GLP-1(7-37)-OH.

100. Use according to any one of the preceding embodiments, wherein said peptide is administered in a composition further comprising one or more pharmaceutically acceptable excipients.

101. Use according to embodiment 22, wherein said composition is in the form of a solid dosage form, such as a tablet or a capsule.

102. Use according to any one of the preceding embodiments, wherein said peptide is administered in a dosage which provides a steady state average plasma concentration of said peptide of 1-1000 nM.

103. Use according to any one of the preceding embodiments, wherein said peptide is administered in a dosage which provides a steady state average plasma concentration of said peptide of 1-300 nM.

104. Use according to any one of the preceding embodiments, wherein said peptide is administered in a dosage which provides a steady state average plasma concentration of said peptide of 10-100 nM 105. Use according to any one of the preceding embodiments, wherein said method comprises prevention and/or treatment of type 2 diabetes or obesity.

EXAMPLES

Preparation of GLP-1 Peptides:

GLP-1 peptides were prepared according to methods known to the person skilled in the art, e.g. as described in example 4 of WO 2006/097537 and in example 2 of WO 2011/080103.

In general, GLP-1 peptides may be prepared by recombinant expression, for example in *E. coli* or *S. cerevisae* (see e.g. WO 2008/034881). Alternatively GLP-1 peptides may be prepared by classical peptide synthesis, e.g., solid phase peptide synthesis using t-Boc or Fmoc chemistry or other well established techniques, see, e.g., Greene and Wuts, "Protective Groups in Organic Synthesis", John Wiley & Sons, 1999 or liquid phase synthesis. Yet alternatively, a combination of recombinant expression and chemical synthesis may be used for the production of GLP-1 peptides (as e.g. described in WO 2009/083549). Chemical modification by GLP-1 peptides may be performed by standard acylation technology as e.g. described in WO 2010/029159.

Preparation of Tablet Compositions Comprising GLP-1 and SNAC:

Tablet compositions comprising GLP-1 peptide and SNAC (sodium N-(8-(2-hydroxybenzoyl)amino)caprylate) were prepared according to methods known to the person skilled in the art by mixing GLP-1 peptide, SNAC, Microcrystalline cellulose (Avicel PH 101), Povidone K 90 (Kollidon 90F), and Magnesium stearate and roller compacting as e.g. described in WO 2008/028859 (preparation of SNAC) and WO 2003/72195, PCT application PCT/EP2013/055362 and PCT application PCT/EP2013/055363 (methods for preparation of GLP-1 peptide/SNAC compositions).

Analysis of Plasma Samples Using LOCI:

The plasma was analysed for active peptide ingredient using a Luminescence Oxygen Channeling Immunoassay (LOCI). The LOCI assay employs donor beads coated with streptavidin and acceptor beads conjugated with a monoclonal antibody binding to a mid-molecular region of active peptide ingredient. The other monoclonal antibody, specific for an N-terminal epitope, was biotinylated. In the assay the three reactants were combined with the active peptide ingredient which form a two-sited immuno-complex. Illumination of the complex releases singlet oxygen atoms from the donor beads which channels into the acceptor beads and trigger chemiluminescence which was measured in the EnVision plate reader. The amount of light was proportional to the concentration of active peptide ingredient and the lower limit of quantification (LLOQ) in plasma was 100 pM.

Alternative Analysis of Plasma Samples Using LC-MS:

The plasma was analysed for active peptide ingredient using LC-MS (Liquid Chromatography-Mass Spectrometry) as known to the person skilled in the art. The LC-MS system consisted of Waters Acquity UPLC system (Waters) consisting of an autosampler (Model Acq-SM), pump (Model Acq-BSM), column oven (Model Acq-SM), detector (Model Acq-TUV) and LTQ Orbitrap XL (Thermo Fisher). RP-HPLC separation was achieved using a linear gradient of acetonitrile in 0.1% formic acid using CSH C18 column (Waters, 1×150 mm) with a flow rate of 0.1 ml/min at 45° C.

Example 1: N-epsilon26-[2-(2-{2-[2-(2-{2-[(S)-4-Carboxy-4-(17-carboxyheptadecanoyl-amino)butyrylamino]ethoxy}ethoxy)acetylamino]ethoxy}ethoxy)acetyl][Aib8,Arg34]GLP-1-(7-37) (GLP-1 peptide 1) in a SNAC Formulation A pharmacokinetic study was carried out to determine plasma half-life of the GLP-1 peptides after p.o. administration to humans.

Subjects were administered p.o. GLP-1 peptide 1 in a SNAC formulation. Blood samples were drawn at pre-defined time points after dosing, and samples were analysed for concentration of the GLP-1 peptide. Based on these measurements plasma concentration versus time profile were plotted and a non-compartmental pharmacokinetic analysis of the data was performed. The variability in plasma concentration was determined as % CV for both $C_{max}$ and AUC. The amount of SNAC in the tablet composition was 300 mg. The results are presented in Table 1.

TABLE 1

| | % CV | |
| --- | --- | --- |
| Dosing regimen of GLP-1 peptide 1 | AUC | Cmax |
| 10 mg/day for 70 days* | 73% (Day 70) | 74% (Day 70) |
| 20 mg/day for 70 days* | 67% (Day 69) | 62% (Day 69) |
| 40 mg/day for 70 days* | 78% (Day 69) | 80% (Day 69) |
| 40 mg/day for 70 days** | 55% (Day 69) | 54% (Day 69) |
| 10 mg, single dose* | 105% | 113% |

*Subjects were healthy.
**Subjects had type 2 diabetes.

These results show that variability in plasma exposure of the GLP-1 peptide was significantly reduced when administering 10, 20 or 40 mg GLP-1 peptide 1 daily for 70 days compared to a single dose of 10 mg GLP-1 peptide 1 to humans.

Example 2: N-epsilon26-[2-(2-{2-[2-(2-{2-[(S)-4-Carboxy-4-(17-carboxyheptadecanoyl-amino)butyrylamino]ethoxy}ethoxy)acetylamino]ethoxy}ethoxy)acetyl][Aib8,Arg34]GLP-1-(7-37) (GLP-1 peptide 1) in SNAC Formulation A pharmacokinetic study was carried out to determine plasma half-life of the GLP-1 peptides after p.o. administration to Beagle dogs.

Dogs were administered p.o. GLP-1 peptide 1 in a SNAC formulation. Blood samples were drawn at predefined time points after dosing, and samples were analysed for concentration of the GLP-1 peptide. Based on these measurements plasma concentration versus time profile were plotted and a non-compartmental pharmacokinetic analysis of the data was performed. The variability in plasma concentration of the GLP-1 peptide was determined as % CV for AUC. The amount of SNAC in the tablet composition was 300 mg. The results are presented in Table 2.

TABLE 2

| Dosing regimen of GLP-1 peptide 1 | % CV AUC |
|---|---|
| 5 mg/day for 7 days | 67% |
| 15 mg, single dose | 131-167% |

These results show that variability in plasma exposure of the GLP-1 peptide was significantly reduced when administering 5 mg GLP-1 peptide 1 daily for 7 days compared to a single dose of 15 mg GLP-1 peptide 1.

Example 3: $N^{\varepsilon 26}$\{2-[2-(2-\{2-[2-(2-\{(S)-4-Carboxy-4-[10-(4-carboxyphenoxy)decanoylamino]-butyrylamino\}ethoxy)ethoxy]acetylamino\}ethoxy)ethoxy]acetyl\}, $N^{\varepsilon 37}$-\{2-[2-(2-\{2-[2-(2-\{(S)-4-carboxy-4-[10-(4-carboxyphenoxy)decanoylamino]butyrylamino\}ethoxy)ethoxy]acetylamino\}ethoxy)ethoxy]acetyl\}-[Aib$^8$,Arg$^{34}$, Lys$^{37}$]GLP-1(7-37)-OH (GLP-1 peptide 2) in SNAC Formulation A pharmacokinetic study was carried out to determine plasma half-life of the GLP-1 peptides after p.o. administration to Beagle dogs.

Dogs were administered p.o. GLP-1 peptide 2 in a SNAC formulation. Blood samples were drawn at predefined time points after dosing, and samples were analysed for concentration of the GLP-1 peptide. Based on these measurements plasma concentration versus time profile were plotted and a non-compartmental pharmacokinetic analysis of the data was performed. The variability in plasma concentration of the GLP-1 peptide was determined as % CV for AUC. The amount of SNAC in the tablet composition was 300 mg. The results are presented in Table 3.

TABLE 3

| Dosing regimen of GLP-1 peptide 2 | % CV AUC |
|---|---|
| 10 mg/day for 7 days | 33% |
| 10 mg, single dose | 67% |

These results show that variability in plasma exposure of the GLP-1 peptide was significantly reduced when administering 10 mg GLP-1 peptide 2 daily for 7 days compared to a single dose of 10 mg GLP-1 peptide 2.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A method for treating type 2 diabetes and/or reducing body weight in a subject in need of such treatment, the method comprising:
orally administering to the subject a therapeutically effective amount of a solid oral dosage form composition comprising a glucagon-like peptide-1 (GLP-1) peptide and an enhancer,
wherein:
(a) the GLP-1 peptide is N-epsilon26-[2-(2-{2-[2-(2-{2-[(S)-4-Carboxy-4-(17-carboxyheptadecanoyl-amino) butyrylamino] ethoxy} ethoxy) acetylamino] ethoxy} ethoxy) acetyl] [Aib8,Arg34] GLP-1-(7-37) (semaglutide); and
(b) the enhancer is sodium N-(8-(2-hydroxybenzoyl) amino) caprylate (SNAC);
wherein semaglutide is the only GLP-1 peptide administered;
wherein the composition is administered daily for a period of 70 days; and
wherein the variability in plasma exposure of said GLP-1 peptide is reduced when compared to a single dose of the GLP-1 peptide.

2. The method according to claim 1, wherein the subject is in need of treatment for both type 2 diabetes and reducing body weight.

3. The method according to claim 2, wherein the composition comprises 200-400 mg of the SNAC.

4. The method according to claim 2, wherein the composition comprises 2-40 mg of the semaglutide.

5. The method according to claim 4, wherein the composition comprises 300 mg of the SNAC.

6. The method according to claim 2, wherein the composition comprises 5-50 mg of the semaglutide.

7. The method according to claim 6, wherein the composition comprises 300 mg of the SNAC.

8. The method according to claim 2, wherein the composition is in the form of a tablet.

9. The method according to claim 2, wherein the subject suffers from obesity.

10. The method according to claim 1, wherein the subject is in need of treatment for type 2 diabetes.

11. The method according to claim 10, wherein the composition comprises 200-400 mg of the SNAC.

12. The method according to claim 10, wherein the composition comprises 2-40 mg of the semaglutide.

13. The method according to claim 12, wherein the composition comprises 300 mg of the SNAC.

14. The method according to claim 13, wherein the composition is in the form of a tablet.

15. The method according to claim 10, wherein the composition comprises 5-50 mg of the semaglutide.

16. The method according to claim 15, wherein the composition comprises 300 mg of the SNAC.

17. The method according to claim 16, wherein the composition is in the form of a tablet.

18. The method according to claim 1, wherein the patient is in need of treatment for reducing body weight.

19. The method according to claim 18, wherein the composition comprises 200-400 mg of the SNAC.

20. The method according to claim 18, wherein the composition comprises 2-40 mg of the semaglutide.

21. The method according to claim 20, wherein the composition comprises 300 mg of the SNAC.

22. The method according to claim 21, wherein the subject suffers from obesity.

23. The method according to claim 21, wherein the composition is in the form of a tablet.

24. The method according to claim 18, wherein the composition comprises 5-50 mg of the semaglutide.

25. The method according to claim 24, wherein the composition comprises 300 mg of the SNAC.

26. The method according to claim 25, wherein the subject suffers from obesity.

27. The method according to claim 25, wherein the composition is in the form of a tablet.

* * * * *